US010107794B2

(12) United States Patent
Kurash et al.

(10) Patent No.: US 10,107,794 B2
(45) Date of Patent: Oct. 23, 2018

(54) METHODS OF USING U2-OS CELLS TO IDENTIFY POTENTIAL SWEET TASTE MODULATORS

(71) Applicant: PepsiCo, Inc., Purchase, NY (US)

(72) Inventors: Yuliya Kurash, Purchase, NY (US); Stephen Gravina, Purchase, NY (US)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 14/890,049

(22) PCT Filed: May 9, 2014

(86) PCT No.: PCT/US2014/037511
§ 371 (c)(1),
(2) Date: Nov. 9, 2015

(87) PCT Pub. No.: WO2014/183044
PCT Pub. Date: Nov. 13, 2014

(65) Prior Publication Data
US 2016/0091488 A1    Mar. 31, 2016

Related U.S. Application Data

(60) Provisional application No. 61/821,943, filed on May 10, 2013.

(51) Int. Cl.
| G01N 33/50 | (2006.01) |
| C07K 14/43 | (2006.01) |
| C07K 14/47 | (2006.01) |
| C07K 14/705 | (2006.01) |
| G01N 33/74 | (2006.01) |
| C07K 14/435 | (2006.01) |

(52) U.S. Cl.
CPC ... *G01N 33/5041* (2013.01); *C07K 14/43504* (2013.01); *C07K 14/47* (2013.01); *C07K 14/705* (2013.01); *G01N 33/5044* (2013.01); *G01N 33/74* (2013.01); *G01N 2333/726* (2013.01); *G01N 2333/912* (2013.01); *G01N 2440/14* (2013.01)

(58) Field of Classification Search
CPC .......... G01N 33/5041; G01N 33/5044; G01N 33/74; G01N 2333/726; G01N 2333/912; G01N 2440/14; C07K 14/43504; C07K 14/47; C07K 14/705
See application file for complete search history.

(56) References Cited

U.S. PATENT DOCUMENTS

| 6,759,206 B1 | 7/2004 | Rubin et al. |
| 7,022,488 B2 | 4/2006 | Servant et al. |
| 7,297,772 B2 | 11/2007 | Zoller et al. |
| 7,402,400 B2 | 7/2008 | Zuker et al. |
| 7,763,431 B1 | 7/2010 | Zoller et al. |
| 7,799,538 B2 | 9/2010 | Lienhard et al. |
| 8,338,115 B2 | 12/2012 | Adler et al. |
| 2002/0160424 A1 | 10/2002 | Adler et al. |
| 2005/0048586 A1 | 3/2005 | Zuker et al. |
| 2005/0244810 A1 | 11/2005 | Egan et al. |
| 2006/0160176 A1 | 7/2006 | Zoller et al. |
| 2008/0039534 A1 | 2/2008 | Radhakrishna et al. |
| 2008/0248996 A1 | 10/2008 | Zoller et al. |
| 2009/0075927 A1 | 3/2009 | Liao et al. |
| 2009/0117563 A1 | 5/2009 | Moyer et al. |
| 2009/0221001 A1 | 9/2009 | Zoller et al. |
| 2009/0317858 A1 | 12/2009 | Hanson |
| 2011/0269235 A1 | 11/2011 | Rawson et al. |
| 2012/0237953 A1 | 9/2012 | Brune et al. |
| 2013/0040316 A1 | 2/2013 | Radhakrishna et al. |
| 2013/0072491 A1 | 3/2013 | Yasuda et al. |
| 2016/0084834 A1 | 3/2016 | Kurash et al. |

FOREIGN PATENT DOCUMENTS

| CN | 101998989 A | 3/2011 |
| RU | 2010110557 A | 9/2011 |
| WO | WO-0003246 A2 | 1/2000 |
| WO | WO-2004055048 A2 | 7/2004 |
| WO | WO-2006040337 A1 | 4/2006 |
| WO | WO-2007047988 A2 | 4/2007 |
| WO | WO-2007121604 A2 | 11/2007 |
| WO | WO-2007147275 A1 | 12/2007 |
| WO | WO-2008014401 A2 | 1/2008 |
| WO | WO-2009008950 A2 | 1/2009 |
| WO | WO-2009025793 A2 | 2/2009 |
| WO | WO-2010088633 A2 | 8/2010 |
| WO | WO-2011067202 A1 | 6/2011 |
| WO | WO-2012102900 A1 | 8/2012 |

OTHER PUBLICATIONS

Extended European Search Report for EP Application No. 14794217.1, European Patent Office, Munich, Germany, dated Nov. 3, 2016, 7 pages.
Gershan, J.A., et al., "Transgene expression in nucleofected cancer cell lines is enhanced by cell division," *Cancer Research* 65(9 Supplement):Abstract 6059, American Association for Cancer Research, United States (2005).
Haasen, D., et al., "G protein-coupled receptor internalization assays in the high-content screening format," *Methods in Enzymology* 414:121-139, Elsevier Inc., United States (2006).
International Preliminary Report on Patentability for International Application No. PCT/US2014/037507, The International Bureau of WIPO dated Nov. 10, 2015, 6 pages.
International Search Report and Written Opinion for International Application No. PCT/US2014/037507, International Searching Authority, dated Oct. 14, 2014, 8 pages.

(Continued)

*Primary Examiner* — Robert Landsman
(74) *Attorney, Agent, or Firm* — Sterne, Kessler, Goldstein and Fox P.L.L.C.

(57) ABSTRACT

Co-expression of T1R2 and T1R3 results in a taste receptor that responds to sweet taste stimuli, including naturally occurring and artificial sweeteners. Cells such as U2-OS, which express a functional sweet receptor, can be used in cell-based assays to detect cellular responses to tastants.

Figure 1A:
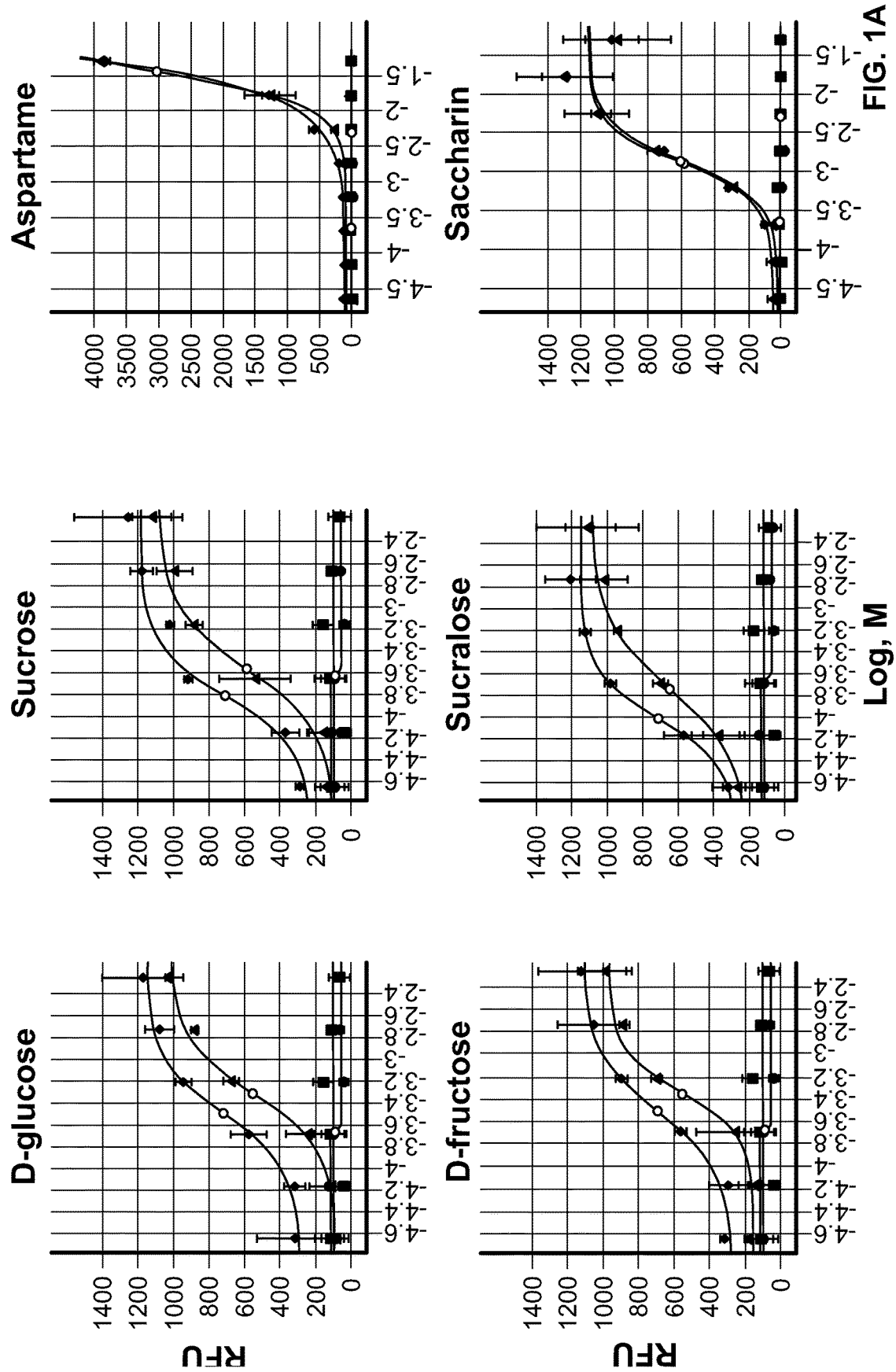

21 Claims, 11 Drawing Sheets
Specification includes a Sequence Listing.

(56) References Cited

OTHER PUBLICATIONS

Lee et al., "Tip60 and HDAC7 Interact with the Endothelin Receptor A and may be Involved in Downstream Signaling," *The Journal of Biological Chemistry* 276(20):16597-16600, American Society for Biochemistry and Molecular Biology, United States, (2001).
Martin, C., et al., "Lipid-mediated release of GLP-1 by mouse taste buds from circumvallate papillae: putative involvement of GPR120 and impact on taste sensitivity," *Journal of Lipid Research* 53(11):2256-2265, American Society for Biochemistry and Molecular Biology, Inc., United States (2012).
Naik N., et al., "Internalization and Recycling of the C5a Anaphylatoxin Receptor: Evidence that the Agonist-mediated Internalization is Modulated by Phosphorylation of the C-terminal Domain," *Journal of Cell Science* 110(Pt 19):2381-2390, Company of Biologists Limited, Great Britain (1997).
Niforou, K.N., et al., "The proteome profile of the human osteosarcoma U2OS cell line," *Cancer Genomics & Proteomics* 5(1):63-78, International Institute of Anticancer Research, Greece (2008).
Ozeck, M., et al., "Receptors for bitter, sweet and umami taste couple to inhibitory G protein signaling pathways," *European Journal of Pharmacology* 489(3):139-149, Elsevier B.V., Netherlands (2004).
Partial Supplementary European Search Report for EP Application No. 14794836.8, European Patent Office, Munich, Germany, dated Nov. 7, 2016, 8 pages.
Van Lith, L.H.C., et al., "C5a-stimulated recruitment β-arrestin2 to the nonsignaling 7-transmembrane decoy receptor C5L2," *Journal of Biomolecular Screening* 14(9):1067-1075, Society for Biomolecular Sciences, United States (2009).
Watts, A.O., et al., "β-Arrestin recruitment and G protein signaling by the atypical human chemokine decoy receptor CCX-CKR," *The Journal of Biological Chemistry* 288(10):7169-7181, American Society for Biochemistry and Molecular Biology, Inc., United States (2013).
Zhao, G.Q., et al., "The Receptors for Mammalian Sweet and Umami Taste," *Cell* 115(3):255-266, Cell Press, United States (2003).
Extended European Search Report for EP Application No. 14794836.8, European Patent Office, Munich, Germany, dated Feb. 17, 2017, 11 pages.
Ueda, T., et al., "Functional Interaction between T2R Taste Receptors and G-Protein α Subunits Expressed in Taste Receptor Cells," *The Journal of Neuroscience* 23(19):7376-7380, Society for Neuroscience, United States (2003).
Wang, T-H., et al., "A novel sweet taste cell-based sensor," *Biosensors and Bioelectronics* 26(2):929-934, Elsevier B.V., Netherlands (2010).
Adler, E., el al., "A Novel Family of Mammalian Taste Receptors," *Cell* 100(6):693-702, Cell Press, United States (2000).
GenBank, "taste receptor type 1 member 2 precursor [*Homo sapiens*]," Accession No. NP_689418.2, accessed at http://www.ncbi.nlm.nih.gov/protein/112789566/, accessed on Jun. 30, 2016, 4 pages.
Genbank, "taste receptor type 1 member 3 precursor [*Homo sapiens*]," Accession No. NP_689414.1, accessed at http://www.ncbi.nlm.nih.gov/protein/NP_689414.1, accessed on Jun. 30, 2016, 4 pages.
International Preliminary Report on Patentability for International Application No. PCT/US2014/037511, The Internatioual Bureau of WIPO, Switzerland, dated Nov. 10, 2015, 7 pages.
International Search Report and Written Opinion for International Application No. PCT/US2014/037511, International Searching Authority, United States, dated Oct. 17, 2014, 10 pages.
Jung, H-J., et al., "Gut-expressed gustducin and taste receptors regulate secretion of glucagon-like peptide-1," *Proc Natl Acad Sci U.S.A.* 104(38):15069-15074, National Academy of Sciences, United States (2007).
Romanov, R.A., "Functional properties of taste bud cells. Mechanisms of afferent neurotransmission in type II taste receptor cells," Progress in the Physiological Sciences, 44:3-15 (2013).
Yee, K.K., et al., "Glucose transporters and ATP-gated $K^+$ ($K_{ATP}$) metabolic sensors are present in type 1 taste receptor 3 (T1r3)-expressing taste cells," Proceedings of the National Academy of Sciences of the USA, 108(13):5431-5436, National Academy of Sciences, United States (2011).
Yu Lin et al., "Practical Feed Flavoring Agents," China Agriculture Press (2012).

SEQUENCE LISTING

```
<160> NUMBER OF SEQ ID NOS: 8

<210> SEQ ID NO 1
<211> LENGTH: 372
<212> TYPE: PRT
<213> ORGANISM: Homo sapiens

<400> SEQUENCE: 1

Met Ala Arg Ser Leu Thr Trp Gly Cys Cys Pro Trp Cys Leu Thr Glu
1               5                   10                  15

Glu Glu Lys Thr Ala Ala Arg Ile Asp Gln Glu Ile Asn Arg Ile Leu
            20                  25                  30

Leu Glu Gln Lys Lys Gln Glu Arg Glu Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Val Gly Tyr Ser Glu Glu Asp Arg Arg Ala Phe Arg Leu
65                  70                  75                  80

Leu Ile Tyr Gln Asn Ile Phe Val Ser Met Gln Ala Met Ile Asp Ala
                85                  90                  95

Met Asp Arg Leu Gln Ile Pro Phe Ser Arg Pro Asp Ser Lys Gln His
```

|     |     |     |     |     | 100 |     |     |     | 105 |     |     |     |     | 110 |     |
| --- | --- | --- | --- | --- | --- | --- | --- | --- | --- | --- | --- | --- | --- | --- | --- |
Ala Ser Leu Val Met Thr Gln Asp Pro Tyr Lys Val Ser Thr Phe Glu
          115                    120                    125

Lys Pro Tyr Ala Val Ala Met Gln Tyr Leu Trp Arg Asp Ala Gly Ile
  130                    135                    140

Arg Ala Cys Tyr Glu Arg Arg Glu Phe His Leu Leu Asp Ser Ala
145                    150                    155                    160

Val Tyr Tyr Leu Ser His Leu Glu Arg Ile Ser Glu Asp Ser Tyr Ile
                    165                    170                    175

Pro Thr Ala Gln Asp Val Leu Arg Ser Arg Met Pro Thr Thr Gly Ile
              180                    185                    190

Asn Glu Tyr Cys Phe Ser Val Lys Lys Thr Lys Leu Arg Ile Val Asp
          195                    200                    205

Val Gly Gly Gln Arg Ser Glu Arg Arg Lys Trp Ile His Cys Phe Glu
  210                    215                    220

Asn Val Ile Ala Leu Ile Tyr Leu Ala Ser Leu Ser Glu Tyr Asp Gln
225                    230                    235                    240

Cys Leu Glu Glu Asn Asp Gln Glu Asn Arg Met Glu Glu Ser Leu Ala
              245                    250                    255

Leu Phe Ser Thr Ile Leu Glu Leu Pro Trp Phe Lys Ser Thr Ser Val
          260                    265                    270

Ile Leu Phe Leu Asn Lys Thr Asp Ile Leu Glu Asp Lys Ile His Thr
         275                    280                    285

Ser His Leu Ala Thr Tyr Phe Pro Ser Phe Gln Gly Pro Arg Arg Asp
  290                    295                    300

Ala Glu Ala Ala Lys Ser Phe Ile Leu Asp Met Tyr Ala Arg Val Tyr
305                    310                    315                    320

Ala Ser Cys Ala Glu Pro Gln Asp Gly Gly Arg Lys Gly Ser Arg Ala
              325                    330                    335

Arg Arg Phe Phe Ala His Phe Thr Cys Ala Thr Asp Thr Gln Ser Val
          340                    345                    350

Arg Ser Val Phe Lys Asp Val Arg Asp Ser Val Leu Ala Arg Tyr Leu
         355                    360                    365

Asp Glu Ile Asn
    370

```
<210> SEQ ID NO 2
<211> LENGTH: 1177
<212> TYPE: DNA
<213> ORGANISM: Homo sapiens

<400> SEQUENCE: 2
```

| | | | |
|---|---|---|---|
| ggatccaggc cggccggtac cgccgccacc atggctagat cccttacttg gcgctgttgt | | | 60 |
| ccttggtgcc tcacggaaga tgaaaaggca gcggctagag tcgatcagga aatcaaccgg | | | 120 |
| attctcttgg agcagaagaa gcaggataga ggagaactca aactgcttct cctcgggcca | | | 180 |
| ggagagagcg gaaaatccac gtttatcaaa cagatgagaa tcattcatgg ggcagggtac | | | 240 |
| agcgaagaag agcgcaaagg gtttcggccc ctcgtctatc agaacatctt tgtctcgatg | | | 300 |
| agggccatga tcgaagcaat ggagcgcctc caaattcctt tctcaaggcc ggagtcgaag | | | 360 |
| caccacgcct cgttggtgat gagccaggac ccgtacaagg tgacaacgtt cgagaaaga | | | 420 |
| tacgcggcag cgatgcagtg gctgtggcgc gatgcgggta tccgggcctg ttacgagagg | | | 480 |
| aggcgagaat tcaccctctt ggactcggca gtatactatc tgtcccatct tgaacggatc | | | 540 |

```
acagaggagg gatacgtgcc tactgctcaa gacgtactgc ggagccgaat gccgacgact    600
gggattaacg agtattgctt ctccgtgcaa aagacaaacc ttaggatcgt agacgtgggc    660
ggacaaaagt cagagcggaa gaagtggatt cactgctttg agaatgtcat tgcgctgatc    720
taccttgcat cgcttagcga gtacgatcag tgtctcgagg agaacaatca ggaaaacagg    780
atgaaagagt ccttggccct gttcgggacc attctggaat tgccctggtt caaatcgaca    840
tcagtgattt tgtttctgaa taagaccgac atcttggaag agaaaatccc cacatcgcat    900
ctcgcgacct atttcccatc atttcagggt cccaaacagg acgcggaagc ggccaagcga    960
ttcatcttgg atatgtacac gcggatgtat accggctgcg tcgacggacc ggagggttcg   1020
aagaaaggtg cgcgatcaag gagactcttc tcgcactata cgtgcgccac tgatacgcag   1080
aatatcagaa aggtattcaa ggacgtccgc gattcggtgc ttgcgcgcta tttggacgaa   1140
atcaatctcc tttaggcggc cgcatattca tggatcc                            1177

<210> SEQ ID NO 3
<211> LENGTH: 1163
<212> TYPE: DNA
<213> ORGANISM: Homo sapiens

<400> SEQUENCE: 3
ggatccaggc cggccggtac cgccgccacc atggctagat cccttacttg gcgctgttgt     60
ccttggtgcc tcacggaaga tgaaaaggca gcggctagat cgatcagga aatcaaccgg    120 attctcttgg agcagaagaa gcaggataga ggagaactca aactgcttct cctcgggcca    180
ggagagagcg gaaaatccac gtttatcaaa cagatgagaa tcattcatgg ggcagggtac    240
agcgaagaag agcgcaaagg gtttcggccc ctcgtctatc agaacatctt tgtctcgatg    300
agggccatga tcgaagcaat ggagcgcctc caaattcctt tctcaaggcc ggagtcgaag    360
caccacgcct cgttggtgat gagccaggac ccgtacaagg tgacaacgtt cgagaaaaga    420
tacgcggcag cgatgcagtg gctgtggcgc gatgcgggta tccggcctg ttacgagagg    480 aggcgagaat tcacctctt ggactcggca gtatactatc tgtcccatct gaacggatc    540 acagaggagg gatacgtgcc tactgctcaa gacgtactgc ggagccgaat gccgacgact    600
gggattaacg agtattgctt ctccgtgcaa aagacaaacc ttaggatcgt agacgtgggc    660
ggacaaaagt cagagcggaa gaagtggatt cactgctttg agaatgtcat tgcgctgatc    720
taccttgcat cgcttagcga gtacgatcag tgtctcgagg agaacaatca ggaaaacagg    780
atgaaagagt ccttggccct gttcgggacc attctggaat tgccctggtt caaatcgaca    840
tcagtgattt tgtttctgaa taagaccgac atcttggaag agaaaatccc cacatcgcat    900
ctcgcgacct atttcccatc atttcagggt cccaaacagg acgcggaagc ggccaagcga    960
ttcatcttgg atatgtacac gcggatgtat accggctgcg tcgacggacc ggagggttcg   1020
aagaaaggtg cgcgatcaag gagactcttc tcgcactata cgtgcgccac tgatacgcag   1080
aatgtcaaat tcgtgtttga cgccgtaacc gatatcatca tcaaggagaa tctcaaggac   1140
tgcggcctgt tctaggcggc cgc                                           1163

<210> SEQ ID NO 4
<211> LENGTH: 1177
<212> TYPE: DNA
<213> ORGANISM: Homo sapiens

<400> SEQUENCE: 4
ggatccaggc cggccggtac cgccgccacc atggcgcgct cccttacgtg gggctgctgt     60
```

```
cctgggtgcc ttactgagga ggaaaagact gcagcgcgca tcgaccagga gatcaaccgc    120
atcttgttgg aacagaagaa gcaggaacga gaagagttga agctcctcct gcttgggcct    180
ggtgaatcgg gaaagtcaac attcatcaag cagatgcgga tcatccacgg ggtgggatat    240
agcgaggagg accgacgggc gtttcgattg cttatctacc agaatatctt tgtgtcgatg    300
caggccatga ttgacgccat ggatcgcttg caaattccat tttcacgacc ggacagcaaa    360
cagcacgcgt cccttgtaat gacgcaagac ccgtacaaag tctcgacatt tgagaaaccc    420
tatgccgtgg cgatgcaata cctttggaga gatgcaggga ttagggcgtg ttatgaacga    480
cggagagagt ttcatctcct cgactccgca gtctactatc tgagccatct ggagcggatc    540
agcgaggata gctacattcc taccgctcaa gacgtgctga gatcaaggat gccgacgact    600
ggcattaacg aatactgctt ctcggtcaag aaaaccaagc tccggatcgt cgatgtcgga    660
gggcagagat cagagaggag aaagtggatt cactgtttcg agaacgtaat cgctttgatc    720
tacttggcga gcctttcgga atacgaccag tgtctggaag agaatgacca ggaaaaccgg    780
atggaggagt cgcttgcact tttctccaca attctggaac tcccctggtt caaatcaacg    840
tccgtgattc tcttcttgaa taagacagac attctcgagg ataagatcca cacgtcccac    900
ctggcgacct actttccatc gtttcagggt ccgaggcgcg acgctgaggc agcgaaatcg    960
ttcatcctcg atatgtatgc cagggtgtat gcctcgtgcg ccgaacccca agatggaggt   1020
aggaaaggat caagagcgag gcgcttcttt gcgcatttca catgcgctac ggatacccag   1080
tcagtgcgat ccgtattcaa agatgtacgc gattcggtcc tcgcccggta tcttgacgag   1140
atcaatctgt tgtaagcggc cgcatattca tggatcc                            1177

<210> SEQ ID NO 5
<211> LENGTH: 1163
<212> TYPE: DNA
<213> ORGANISM: Homo sapiens

<400> SEQUENCE: 5
ggatccaggc cggccggtac cgccgccacc atggcgcgct cccttacgtg gggctgctgt     60
cctgggtgcc ttactgagga ggaaaagact gcagcgcgca tcgaccagga gatcaaccgc    120
atcttgttgg aacagaagaa gcaggaacga gaagagttga agctcctcct gcttgggcct    180
ggtgaatcgg gaaagtcaac attcatcaag cagatgcgga tcatccacgg ggtgggatat    240
agcgaggagg accgacgggc gtttcgattg cttatctacc agaatatctt tgtgtcgatg    300
caggccatga ttgacgccat ggatcgcttg caaattccat tttcacgacc ggacagcaaa    360
cagcacgcgt cccttgtaat gacgcaagac ccgtacaaag tctcgacatt tgagaaaccc    420
tatgccgtgg cgatgcaata cctttggaga gatgcaggga ttagggcgtg ttatgaacga    480
cggagagagt tcatctcct cgactccgca gtctactatc tgagccatct ggagcggatc    540
agcgaggata gctacattcc taccgctcaa gacgtgctga gatcaaggat gccgacgact    600
ggcattaacg aatactgctt ctcggtcaag aaaaccaagc tccggatcgt cgatgtcgga    660
gggcagagat cagagaggag aaagtggatt cactgtttcg agaacgtaat cgctttgatc    720
tacttggcga gcctttcgga atacgaccag tgtctggaag agaatgacca ggaaaaccgg    780
atggaggagt cgcttgcact tttctccaca attctggaac tcccctggtt caaatcaacg    840
tccgtgattc tcttcttgaa taagacagac attctcgagg ataagatcca cacgtcccac    900
ctggcgacct actttccatc gtttcagggt ccgaggcgcg acgctgaggc agcgaaatcg    960
```

| | |
|---|---|
| ttcatcctcg atatgtatgc cagggtgtat gcctcgtgcg ccgaacccca agatggaggt | 1020 |
| aggaaaggat caagagcgag gcgcttcttt gcgcatttca catgcgctac ggatacccag | 1080 |
| aatgtcaaat tcgtgtttga cgccgtaacc gatatcatca tcaaggagaa tctcaaggac | 1140 |
| tgcggcctgt tctaggcggc cgc | 1163 |

<210> SEQ ID NO 6
<211> LENGTH: 1163
<212> TYPE: DNA
<213> ORGANISM: Homo sapiens

<400> SEQUENCE: 6

| | |
|---|---|
| ggatccaggc cggccggtac cgccgccacc atggctagat cccttacttg cgctgttgt | 60 |
| ccttggtgcc tcacggaaga tgaaaaggca gcggctagag tcgatcagga aatcaaccgg | 120 |
| attctcttgg agcagaagaa gcaggataga ggagaactca aactgcttct cctcgggcca | 180 |
| ggagagagcg gaaaatccac gtttatcaaa cagatgagaa tcattcatgg ggcagggtac | 240 |
| agcgaagaag agcgcaaagg gtttcggccc ctcgtctatc agaacatctt tgtctcgatg | 300 |
| agggccatga tcgaagcaat ggagcgcctc caaattcctt tctcaaggcc ggagtcgaag | 360 |
| caccacgcct cgttggtgat gagccaggac ccgtacaagg tgcaacgtt cgagaaaaga | 420 |
| tacgcggcag cgatgcagtg gctgtggcgc gatgcgggta tccgggcctg ttacgagagg | 480 |
| aggcgagaat tcacctcttt ggactcggca gtatactatc tgtcccatct gaacggatc | 540 |
| acagaggagg gatacgtgcc tactgctcaa gacgtactgc ggagccgaat gccgacgact | 600 |
| gggattaacg agtattgctt ctccgtgcaa aagacaaacc ttaggatcgt agacgtgggc | 660 |
| ggacaaaagt cagagcggaa gaagtggatt cactgctttg agaatgtcat tgcgctgatc | 720 |
| taccttgcat cgcttagcga gtacgatcag tgtctcgagg agaacaatca ggaaaacagg | 780 |
| atgaaagagt ccttggccct gttcgggacc attctggaat tgccctggtt caaatcgaca | 840 |
| tcagtgattt tgtttctgaa taagaccgac atccttgaag agaaaatccc cacatcgcat | 900 |
| ctcgcgacct atttcccatc atttcagggt cccaaacagg acgcggaagc ggccaagcga | 960 |
| ttcatcttgg atatgtacac gcggatgtat accggctgcg tcgacggacc ggagggttcg | 1020 |
| aacctcaaga agaagataa ggaaatctac agccatatga cttgtgcgac cgacacgcag | 1080 |
| aatgtgaagt ttgtatttga cgcggtaact gacatcatca ttaaggaaaa ccttaaagat | 1140 |
| tgtggtcttt tctgagcggc cgc | 1163 |

<210> SEQ ID NO 7
<211> LENGTH: 1163
<212> TYPE: DNA
<213> ORGANISM: Homo sapiens

<400> SEQUENCE: 7

| | |
|---|---|
| ggatccaggc cggccggtac cgccgccacc atggcgcgct cccttacgtg gggctgctgt | 60 |
| ccctggtgcc ttactgagga ggaaaagact gcagcgcgca tcgaccagga gatcaaccgc | 120 |
| atcttgttgg aacagaagaa gcaggaacga gaagagttga agctcctcct gcttgggcct | 180 |
| ggtgaatcgg gaaagtcaac attcatcaag cagatgcgga tcatccacgg ggtgggatat | 240 |
| agcgaggagg accgacgggc gtttcgattg cttatctacc agaatatctt tgtgtcgatg | 300 |
| caggccatga ttgacgccat ggatcgcttg caaattccat tttcacgacc ggacagcaaa | 360 |
| cagcacgcgt cccttgtaat gacgcaagac ccgtacaaag tctcgacatt tgagaaaccc | 420 |
| tatgccgtgg cgatgcaata ccttggaga gatgcaggga ttagggcgtg ttatgaacga | 480 |

```
cggagagagt tcatctcct cgactccgca gtctactatc tgagccatct ggagcggatc    540
agcgaggata gctacattcc taccgctcaa gacgtgctga gatcaaggat gccgacgact    600
ggcattaacg aatactgctt ctcggtcaag aaaaccaagc tccggatcgt cgatgtcgga    660
gggcagagat cagagaggag aaagtggatt cactgtttcg agaacgtaat cgctttgatc    720
tacttggcga gcctttcgga atacgaccag tgtctggaag agaatgacca ggaaaaccgg    780
atggaggagt cgcttgcact tttctccaca attctggaac tcccctggtt caaatcaacg    840
tccgtgattc tcttcttgaa taagacagac attctcgagg ataagatcca cacgtcccac    900
ctggcgacct actttccatc gtttcagggt ccgaggcgcg acgctgaggc agcgaaatcg    960
ttcatcctcg atatgtatgc cagggtgtat gcctcgtgcg ccgaaccccg agatggaggt   1020
aacctcaaga aagaagataa ggaaatctac agccatatga cttgtgcgac cgacacgcag   1080
aatgtgaagt ttgtatttga cgcggtaact gacatcatca ttaaggaaaa ccttaaagat   1140
tgtggtcttt tctgagcggc cgc                                            1163

<210> SEQ ID NO 8
<211> LENGTH: 1163
<212> TYPE: DNA
<213> ORGANISM: Homo sapiens

<400> SEQUENCE: 8
ggatccaggc cggccggtac cgccgccacc atggcgcgct cccttacgtg gggctgctgt     60
ccctggtgcc ttactgagga ggaaaagact gcagcgcgca tcgaccagga gatcaaccgc    120
atcttgttgg aacagaagaa gcaggaacga gaagagttga agctcctcct gcttgggcct    180
ggtgaatcgg gaaagtcaac attcatcaag cagatgcgga tcatccacgg ggtgggatat    240
agcgaggagg accgacgggc gtttcgattg cttatctacc agaatatctt tgtgtcgatg    300
caggccatga ttgacgccat ggatcgcttg caaattccat tttcacgacc ggacagcaaa    360
cagcacgcgt cccttgtaat gacgcaagac ccgtacaaag tctcgacatt tgagaaaccc    420
tatgccgtgg cgatgcaata cctttggaga gatgcaggga ttagggcgtg ttatgaacga    480
cggagagagt tcatctcct cgactccgca gtctactatc tgagccatct ggagcggatc    540
agcgaggata gctacattcc taccgctcaa gacgtgctga gatcaaggat gccgacgact    600
ggcattaacg aatactgctt ctcggtcaag aaaaccaagc tccggatcgt cgatgtcgga    660
gggcagagat cagagaggag aaagtggatt cactgtttcg agaacgtaat cgctttgatc    720
tacttggcga gcctttcgga atacgaccag tgtctggaag agaatgacca ggaaaaccgg    780
atggaggagt cgcttgcact tttctccaca attctggaac tcccctggtt caaatcaacg    840
tccgtgattc tcttcttgaa taagacagac attctcgagg ataagatcca cacgtcccac    900
ctggcgacct actttccatc gtttcagggt ccgaggcgcg acgctgaggc agcgaaatcg    960
ttcatcctcg atatgtatgc cagggtgtat gcctcgtgcg ccgaaccccg agatggaggt   1020
aggaaaggat caagagcgag gcgcttcttt gcgcatttca catgcgctac ggatacccag   1080
tcagtgcgat ccgtattcaa agatgtacgc gattcggtcc tcgcccggta tcttgacgag   1140
tgcgggctgt attaagcggc cgc                                            1163
```

METHODS OF USING U2-OS CELLS TO IDENTIFY POTENTIAL SWEET TASTE MODULATORS

Each reference cited in this disclosure is incorporated herein in its entirety.

This application incorporates by reference a 13.7 kb text file created on May 5, 2014 and named "056943.01231sequencelisting.txt," which is the sequence listing for this application.

TECHNICAL FIELD

This disclosure relates generally to cell lines and assays that can be used to identify sweet taste receptor modulators.

BRIEF DESCRIPTION OF THE DRAWINGS

FIG. 1A-B. $Ca^{(2+)}$ response to sweet-tasting compounds. FIG. 1A, Dose-response curves of $Ca^{(2+)}$-release in JUMP-IN T-REX U2-OS with (diamond) and without (triangle) T1R3/T1R2/Gα15 activation (n=3 experiments). FIG. 1B, Effects of lactisole and U73122 on $Ca^{(2+)}$ response in JUMP-IN T-REX U2-OS cells (mean±SD).

FIG. 2. Graphs showing effect of Gals protein on U2-OS response to 100 mM sucralose. U2-OS cells were transiently transfected with 3, 6 and 12 μl/40,000 cells of BacMam encoding G protein, gustducin (Gα15) during 24 h (left) or 48 h (right).

FIG. 3. Graph showing effect of natural sugars (glucose, fructose, and sucrose) at 100 mM on U2-OS cells transfected with 0 or 6 μl/40,000 cells of BacMam encoding Gα15.

FIG. 4. Graph showing that sweet receptor activates pERK1/2 in U2-OS cells upon treatment with glucose at 100 mM. Treatment of U2-OS cells with lactisole (20 mM, left bars) blocked D-glucose-mediated activation of pERK1/2.

FIG. 5. Graph demonstrating that transfection of U2-OS cells with Gα15 (6 μl/40,000 cells) significantly increases pERK1/2 activation, which was blocked by PLCβ2 inhibitor U73122 (10 μM).

FIG. 6. Graph showing pERK1/2 activation upon treatment with D-glucose and maltose in U2-OS cells transfected with Gα15 (6 μl/40,000 cells).

FIG. 7. Graph showing pERK1/2 activation upon treatment with different sugars in U2-OS cells transfected with Gα15 (6 μl/40,000 cells).

FIG. 8A-B. TRANSFLUOR assay. FIG. 8A, Formation of green fluorescent vesicles in TRANSFLUOR U2-OS cells transfected with BacMam encoding Gα15. Nuclei are counterstained blue with HOECHST 33342. FIG. 8B, Quantification of T1R2/T1R3 internalization in TRANSFLUOR model (means±SD).

FIG. 9A-B. U2-OS cells express endogenous sweet receptor T1R2/T1R3. FIG. 9A, U2-OS cells were fixed and processed for indirect immunofluorescence with antibodies against sweet receptor T1R2 and T1R3. All images were acquired with a 20× objective using ImageXpress Micro automated microscope. HOECHST 33342 staining is pseudo-colored blue, and antibody-specific staining is pseudo-colored green. FIG. 9B. Western blot of T1R2 in U2-OS and NCI-H716 cells. Cells were lysed in RIPA buffer (50 mM Tris-HCl pH 7.5, 150 mM NaCl, 1% NP-40, 5 mM EDTA, 0.1% SDS, and 10 μg/ml proteinase inhibitors). After freeze-thaw cycles, loading buffer was added at final concentration 2×, samples were heated at 95° C. for 10 minutes and spun in a microcentrifuge for 10 min at highest speed at RT. Supernatant was loaded on gel for analysis by immunoblotting. The primary antibodies for T1R2 and GAPDH were from ThermoFisher.

DETAILED DESCRIPTION

Co-expression of T1R2 and T1R3 results in a taste receptor that responds to sweet taste stimuli, including naturally occurring and artificial sweeteners. Sweet ligands bind to the T1R2/T1R3 receptor and activate G-protein pathway transduction, which includes receptor internalization and intracellular calcium mobilization, as well as induction of down-stream targets such as the phosphorylation of ERK1/2 (Jang et al., "Gut-expressed gustducin and taste receptors regulate secretion of glucagon-like peptide-1," Proc Natl Acad Sci USA. 2007 Sep. 18; 104(38):15069-74).

Any cell that comprises or can be engineered to comprise a functional sweet taste receptor can be used in the disclosed assay. In some embodiments, the cells express one or more sweet taste receptors. In some embodiments, the cells are genetically modified to express or to overexpress sweet taste receptors. For example, a cell can be genetically modified by introducing an exogenous nucleic acid encoding T1R2 and T1R3 or two separate exogenous nucleic acids encoding T1R2 and T1R3, respectively. Amino acid sequences for these proteins are known; e.g., GenBank Accession No. NP_689418.2 (T1R2) and GenBank Accession No. NP_689414.1 (T1R3).

Cells can be engineered to express T2R14, T1R2/T1R3, an α-gustducin, and/or GLUT4 using methods well known in the art. GLUT4 is described, inter alia, in U.S. Pat. No. 7,799,538 and references cited therein. See U.S. Pat. No. 8,338,115 and references cited therein and Adler et al., Cell 100, 693-702, 2000 for descriptions of α-gustducin.

In some embodiments, cells are genetically modified to overexpress an α-gustducin (e.g., Gα16, Gα15, Gα16gust25, Gα15gust25, Gα16gust44, Gα15gust44, Gα15-i/3-5), which increases the sensitivity of the assays. SEQ ID NO:1 is the amino acid sequence of Gα15. Nucleotide sequences which can be used to express Gα16 (SEQ ID NO:2), Gα16gust25 (SEQ ID NO:3), Gα15 (SEQ ID NO:4), Gα15gust25 (SEQ ID NO:5), Gα16gust44 (SEQ ID NO:6), Gα15gust44 (SEQ ID NO:7), and Gα15-i/3-5 (SEQ ID NO:8) are provided in the sequence listing; however, any nucleotide sequences which encode these α-gustducins can be used to express them.

In some embodiments, U2-OS cells are used, as described below. Human U2-OS cells (ATCC catalog # HTB-96) express a functional sweet receptor (FIGS. 9A-B). U2-OS cells can therefore be used to detect cellular responses to potential sweet tastants by contacting U2-OS cells with a test compound and measuring sweet taste receptor activity. A variety of functional assays can be used, including measurement of changes in intracellular calcium concentration (e.g., Fluorometric Imaging Plate Reader-based $Ca^{2+}$ mobilization assay, FLIPR), pERK1/2 activation (e.g., high content imaging, HCl), and receptor internalization (e.g., TRANSFLUOR). A change in sweet taste receptor activity by a sweetener in the presence of a test compound indicates modulation of the sweet taste receptor by the test compound, thereby identifying a sweet taste modulator (e.g., a molecule which itself provides a sweet taste, a molecule which blocks some or all of a bitter taste, a molecule which enhances the sweet taste of another molecule). An increase in sweet taste receptor activity indicates that the test compound is a sweet taste modulator. Sweet taste modulators can be included in various consumables, including foods, beverages, and pharmaceuticals.

Other cells that can be used in the disclosed assay include, but are not limited to, 1A2, ARH-77, RWPE-1, WI-38, EJM, NCI-H1155, L-1236, NCI-H526, JM1, SHP-77, SNU-878, NCI-H2196, C3A, CA46, SNU-466, KS-1, SNU-738, MOLP-2, HDLM-2, Pfeiffer, HCC-15, Alexander cells, L-540, KMS-12-BM, JK-1, NCI-H1092, SW 1990, NCI-H1184, SU-DHL-1, Hep 3B2.1-7, P3HR-1, NCI-H2029, SU-DHL-5, SNU-1, MOLP-8, SUP-M2, MONO-MAC-1, SNU-1040, KYM-1, HEC-59, HCC1569, OCI-LY3, Hs 819.T, DU4475, CI-1, S-117, OVCAR-8, SNU-626, HL-60, SUIT-2, T3M-4, RKO, MOR/CPR, DK-MG, GA-10, OCUM-1, HCT-15, HT, MONO-MAC-6, G-402, Toledo, COV362, SU-DHL-8, Daoy, NCI-H1435, LS513, Hs 839.T, Hs 172.T, BT-483, KMS-21BM, AGS, NCI-H2172, LC-1/sq-SF, SNU-201, NUGC-4, SK-HEP-1, SUP-B15, SNU-5, HT-1197, SUP-T1, AMO-1, KU812, AN3 CA, AML-193, VMRC-RCW, HLE, HuH28, Hs 751.T, NCI-H2110, MEG-01, MV-4-11, Hep G2, KYSE-30, KALS-1, BICR 6, RMUG-S, JHH-6, Ki-JK, IST-MES1, HCC-95, HPB-ALL, HSC-3, 697, LOU-NH91, KARPAS-299, GI-1, COLO 792, SK-N-FI, D341 Med, HGC-27, SR-786, COLO-818, MHH-CALL-2, SF126, NCI-H322, A-253, NCI-H1623, MCF7, HCC-44, FU97, OCI-LY-19, Hs 766T, NCI-H522, RL, HCC1428, RPMI 6666, U-937, NCI-H460, SW 1088, NCI-H1792, NCI-H1693, UACC-257, JHUEM-2, HuT 78, UACC-893, NCI-H929, A-704, OV56, LN-229, OE19, SK-MEL-24, RD-ES, NCI-H211, KCI-MOH1, NCI-H1963, Hs 706.T, ChaGo-K-1, EPLC-272H, OPM-2, KHM-1B, A549, HuG1-N, NCI-H508, MHH-CALL-3, SNU-1076, A3/KAW, MEL-HO, TO 175.T, Caki-1, Hs 936.T, SK-LU-1, WM-983B, K-562, EFE-184, SNU-520, NCI-H2291, HCC-1195, ABC-1, KE-39, NH-6, HCC2218, CMK, RS4;11, KYSE-450, OV7, KYSE-510, SK-UT-1, SNU-C1, OE33, P12-ICHIKAWA, DLD-1, COV434, HuNS1, SNU-899, SW480, COLO-678, LU99, KOPN-8, NCI-H2227, SW1463, Hs 675.T, JHH-4, NCI-H1703, HEC-1-A, BDCM, MIA PaCa-2, PC-3, TE-15, PK-45H, MKN-45, HCC-366, CAL-29, HEC-50B, CPC-N, KMRC-20, SW1116, EOL-1, COLO 205, EHEB, YD-38, MC116, SK-N-BE(2), BV-173, NCI-H2347, LU65, RT4, U-87 MG, LK-2, KP-N-YN, HEC-251, NCI-H1651, GP2d, RERF-LC-MS, NB-4, NCI-H2286, SNU-61, T-47D, huH-1, KYSE-180, ST486, SW 1353, M-07e, KASUMI-1, YH-13, NCI-H28, GAMG, JeKo-1, GOS-3, SNU-324, PA-TU-8902, MFE-280, SNU-245, NALM-1, RERF-LC-Sq1, BICR 22, ZR-75-1, COR-L23, SW579, COR-L88, KM12, Hs 611.T, OUMS-23, RERF-LC-Ad1, NCI-H1385, SK-LMS-1, COLO-320, BL-70, GRANTA-519, MCAS, Panc 08.13, AM-38, KMS-11, SIG-M5, SNU-407, JHOS-2, OVCAR-4, Set-2, OV-90, MeWo, HEL, HT-29, MDA-MB-231, TOV-21G, NCI-H1355, KMS-27, NALM-6, KMS-26, Caov-4, KASUMI-2, UACC-62, U266B1, Hs 695T, HT55, BICR 31, TCC-PAN2, KMS-20, Hs 578T, RI-1, Hs 606.T, NCI-H1341, THP-1, BCP-1, Hs 737.T, SW1417, MOLT-4, Raji, ESS-1, MEL-JUSO, SH-10-TC, Hs 683, ME-1, EB2, PLC/PRF/5, NCI-H1339, A4/Fuk, SEM, HEC-265, IST-MES2, KE-97, NCI-H1437, COLO-704, NCI-H1915, TE-5, NCI-H2023, NCI-H82, T1-73, SNU-840, HuT 102, NCI-H1944, KYSE-520, Kasumi-6, 1321N1, Hs 742.T, IM95, PL45, CL-40, WM1799, KMM-1, SNU-449, JHUEM-1, KARPAS-620, Loucy, SNU-1079, Daudi, HCC-56, HSC-2, COR-L47, PA-TU-89885, OAW28, COR-L311, L-363, Malme-3M, NOMO-1, Hs 870.T, SU-DHL-10, Hs 229.T, NCI-H810, KYSE-410, RPMI-8402, SNU-175, EBC-1, RVH-421, K029AX, PA-TU-8988T, LXF-289, OVSAHO, CAL-12T, Hs 940.T, MM1-S, SUP-HD1, LNCaP clone FGC, HSC-4, NU-DHL-1, NCI-H2228, BEN, CAL-78, Sq-1, NCI-H1793, SNU-C2A, MDA-MB-134-VI, COV318, KE-37, TYK-nu, MOTN-1, T98G, SW837, EB1, Becker, PE/CA-PJ34 (clone C12), Hs 616.T, NCI-H446, WM-88, CHP-126, Calu-1, SNU-283, NCI-H1573, SW 1271, SNU-16, JHOS-4, ACHN, Calu-3, KMRC-1, SW 1783, TE-11, TE-9, HuH-6, P31/FUJ, HT-1376, NCI-H520, 786-O, KNS-60, Caki-2, OVK18, PL-21, NCI-H2452, JURL-MK1, TEN, JHH-7, MDA-MB-157, Calu-6, RKN, NUGC-2, ONS-76, J82, OUMS-27, SNU-1196, Hs 739.T, RPMI-7951, NCI-H854, JHH-5, JVM-2, Hey-A8, 5637, KYSE-140, Capan-2, KYSE-150, HEC-1-B, BICR 16, HEL 92.1.7, MHH-NB-11, SNU-387, SK-OV-3, SK-MEL-28, IGROV1, ML-1, HLF-a, CHL-1, YKG1, A-204, OCI-M1, 8505C, JVM-3, NCI-H647, DB, COLO-800, PK-59, FaDu, HLF, OVMANA, EFO-27, PF-382, NCI-H747, LS123, SU-DHL-6, SJRH30, PANC-1, NCI-H2342, KM-H2, DND-41, HH, HuCCT1, F-36P, DMS 454, Hs 274.T, AU565, NCI-H1666, EN, RH-41, NCI-H1373, NCI-H838, SK-MEL-30, MOLM-6, DEL, NCI-H226, NCI-H1648, NCI-H661, 143B, Mino, C32, KMS-34, NCI-H1694, SK-ES-1, UACC-812, GDM-1, NCI-H23, Panc 02.03, CCF-STTG1, LOX IMVI, SJSA-1, MDST8, PK-1, NCI-H716, SU-DHL-4, MPP 89, MJ, COLO 829, PE/CA-PJ15, HD-MY-Z, BxPC-3, WM-793, COLO 668, T84, JHOM-1, PEER, LS411N, GMS-10, KMBC-2, RMG-I, KELLY, SNU-761, NALM-19, HEC-151, G-361, OVTOKO, A-498, SW 900, LCLC-103H, FTC-133, QGP-1, Reh, CMK-11-5, NU-DUL-1, BT-20, Hs 600.T, Hs 604.T, KATO III, SNU-410, NCI-H2126, SK-MEL-5, MDA-MB-468, AsPC-1, HUP-T3, KP-N-SI9s, L-428, SNU-1105, HUP-T4, 769-P, LMSU, NCI-H1869, NCO2, MOLM-16, CAL 27, HCC70, NCI-H1930, COV644, Hs 863.T, HCC-2279, D283 Med, Hs 944.T, HCC1599, MDA-MB-415, HCC2157, NCI-H1618, SNU-308, HCC1954, DMS 153, HPAF-II, T24, CJM, VM-CUB1, UM-UC-3, LAMA-84, NCI-H1734, JHH-2, VMRC-RCZ, MFE-319, MDA-MB-453, SNU-503, TOV-112D, B-CPAP, GSU, HCC-78, NCI-H2171, CAMA-1, HEC-108, HCC4006, CAL-85-1, NCI-H2122, COLO-699, NCI-H196, LUDLU-1, SW 780, RPMI 8226, LP-1, PC-14, HuTu 80, T.T, SW948, 22Rv1, HARA, NCI-H596, IPC-298, SCaBER, NCI-H1838, NB-1, Hs 934.T, Hs 895.T, DMS 114, KYSE-70, KP-3, KP4, DAN-G, NCI-H2009, OC 316, SCC-25, U-138 MG, RCC10RGB, MFE-296, NCI-H1755, RERF-LC-KJ, 8305C, WSU-DLCL2, ES-2, MSTO-211H, SCC-15, ZR-75-30, PSN1, SNU-423, NCI-H2106, TE-1, UT-7, KMS-28BM, NCI-H2081, SK-MM-2, COLO 741, OC 314, HCC1395, MOLT-13, LN-18, Panc 10.05, PE/CA-PJ41 (clone D2), Hs 746T, CW-2, SKM-1, NUGC-3, TE-10, NCI-H358, NCI-H69, BFTC-909, HOS, BICR 18, NCI-H1395, OVKATE, Hs 698.T, EFM-19, COLO-783, MHH-CALL-4, ACC-MESO-1, NCI-H1436, KP-N-RT-BM-1, SK-MEL-31, NCI-H1105, CAL-51, YD-15, NCI-H2085, NCI-H2444, HCC1187, Hs 939.T, CAL-120, SCC-9, TUHR14TKB, KMRC-2, KG-1-C, ECC10, CGTH-W-1, NCI-H841, C2BBe1, SUP-T11, RCH-ACV, CADO-ES1, JURKAT, 647-V, SK-MEL-2, MDA-MB-175-VII, MKN74, SNU-C4, LCLC-97TM1, SCC-4, BHY, IGR-37, KYO-1, Hs 281.T, TT, TUHR4TKB, HT-1080, NCI-H660, TE 441.T, LS1034, KNS-42, Panc 04.03, HCC1419, AZ-521, SNG-M, NCI-N87, G-292, clone A141B1, KPL-1, MDA-MB-361, CL-14, NCI-H2170, HuH-7, RD, NCI-H2066, IGR-1, TE-14, VCaP, BL-41, SNU-620, SK-MES-1, MEC-2, NCI-H1299, IGR-39, RT112/84, SF-295, DV-90, A2780, BICR 56, NCI-H510, NCI-H2141, YD-8, NCI-H2405, TF-1, MEC-1, CCK-81, NCI-H1048, Hs 822.T, NCI-H2052, K052, CAL-54, Hs 840.T, SW620, SK-CO-1, BT-474, CL-11, KNS-62, NCI-H1650, G-401, MOLT-16, SNU-398, COLO-680N, EM-2, Hs 294T, CAL-62, KMRC-3, A101D, KG-1, BT-549, HT115, A-375, SW-1710, WM-115, KLE, JHUEM-3, MKN7, CHP-212, HCC202, BC-3C, NCI-H1568, KMS-18, PE/CA-PJ49, COLO-849, SIMA, OCI-AML3, GSS, EC-GI-10, EFO-21, RCM-1, DMS 273, KU-19-19, RERF-GC-1B, SH-4, SK-MEL-3, RERF-LC-Ad2, M059K, JHOM-2B, MDA PCa 2b, Hs 852.T, RL95-2, Panc 03.27, SNU-216, Panc 02.13, CFPAC-1, SK-N-SH, OCI-AML2, LoVo, SBC-5, NCI-H1876, NCI-H441, SK-N-AS, COR-L24, HCC38, NCI-H1781, DOHH-2, NCI-H1563, U-251 MG, HPAC, JIMT-1, U-2 OS, A-673, TC-71, NCI-H650, NIH:OVCAR-3, CAS-1, JL-1, SK-MEL-1, MDA-MB-4355, Ishikawa (Heraklio) 02 ER-, TE 617.T, SU.86.86, RERF-LC-AI, TT2609-C02, LS 180, YAPC, HDQ-P1, KNS-81, FU-OV-1, KP-2, DMS 53, SNU-1272, Detroit 562, 42-MG-BA, L3.3, COLO-679, NCI-H2087, NCI-H2030, GCT, NCI-H889, Caov-3, MDA-MB-436, NCI-H524, MKN1, KCL-22, Capan-1, CML-T1, H4, NCI-H727, Hs 343.T, MHH-ES-1, NMC-G1, HCC-1171, REC-1, Hs 618.T, A172, YD-10B, SW48, MUTZ-5, TE-6, JHH-1, HCT 116, TE-4, IA-LM, MG-63, NCI-H1975, TALL-1, HCC1806, HMCB, SCLC-21H, HCC1500, CL-34, Panc 05.04, SW403, TM-31, HCC1937, JMSU-1, DMS 79, SNB-19, NCI-H1836, Li-7, HCC827, 639-V, MOLM-13, SK-BR-3, IMR-32, TUHR10TKB, OAW42, SK-N-MC, TGBC11TKB, NCI-H1581, EFM-192A, YMB-1, HCC2935, ECC12, HCC-33, DU 145, NCI-H146, SNU-1214, SNU-1077, 23132/87, HT-144, SNU-182, Hs 888.T, SNU-475, GCIY, Hs 729, JHOC-5, SW 1573, HEC-6, OCI-AMLS, Hs 688(A).T, Hs 821.T, PCM6, RT-112, SK-N-DZ, SNU-478, SNU-119, HCC1143, NCI-H209, 8-MG-BA, COR-L105, COR-L95, SNU-46, COV504, CAL-148, SNU-05, DBTRG-05MG, BHT-101, WM-266-4, BFTC-905, KYSE-270, TE-8, SNU-213, and SH-SYSY.

Test Compounds

Test compounds can be naturally occurring or synthetically produced. Proteins, polypeptides, peptides, polysaccharides, small molecules, and inorganic salts are examples of test compounds that can be screened using methods disclosed herein.

Any nucleic acid molecule that encodes these proteins can be introduced into a cell. The nucleic acid can be stably or transiently introduced into the cell. The exogenous nucleic acid can be in a construct or vector that comprises a promoter that is operably linked to the coding portion of the nucleic acid.

Cells(s) can be grown on an appropriate substrate, such as a multi-well plate, a tissue culture dish, a flask, etc.; see Examples 1 and 2, below.

Screening Methods

In some embodiments, methods of identifying a sweet taste modulator comprise contacting a cell with a test compound and measuring sweet taste receptor activity. A change in sweet taste receptor activity by the test compound indicates modulation of the sweet taste receptor by the test compound, thereby identifying the test compound as a sweet taste modulator.

Sweet taste receptor activity can be measured quantitatively or qualitatively by any means standard that is in the art, including assays for G protein-coupled receptor activity, changes in the level of a second messenger in the cell, formation of inositol triphosphate ($IP_3$) through phospholipase C-mediated hydrolysis of phosphatidylinositol, changes in cytoplasmic calcium ion levels, β-arrestin recruitment, and the like. Examples of such assays are provided in the specific examples, below.

Binding activity can also be used to measure taste receptor activity, for example, via competitive binding assay or surface plasmon resonance. Receptor internalization and/or receptor desensitization can also be measured, as is known in the art. Receptor-dependent activation of gene transcription can also be measured to assess taste receptor activity. The amount of transcription may be measured by using any method known to those of skill in the art. For example, mRNA expression of the protein of interest may be detected using PCR techniques, microarray or Northern blot. The amount of a polypeptide produced by an mRNA can be determined by methods that are standard in the art for quantitating proteins in a cell, such as Western blotting, ELISA, ELISPOT, immunoprecipitation, immunofluorescence (e.g., FACS), immunohistochemistry, immunocytochemistry, etc., as well as any other method now known or later developed for quantitating protein in or produced by a cell.

Physical changes to a cell can also be measured, for example, by microscopically assessing size, shape, density or any other physical change mediated by taste receptor activation. Flow cytometry can also be utilized to assess physical changes and/or determine the presence or absence of cellular markers.

In some embodiments, sweet taste receptor activity is measured by detecting the level of an intracellular second messenger in the cell (e.g., cAMP, cAMP, cGMP, NO, CO, H2S cGMP, DAG, IP3). In some embodiments, sweet taste receptor activity is measured by detecting the level of intracellular calcium. In some embodiments, the sweet taste receptor activity is binding activity.

In any of these embodiments, the cell can modified to overexpress the sweet taste receptor and or Gα15, as described below.

Those skilled in the art will appreciate that there are numerous variations and permutations of the above described embodiments that fall within the scope of the appended claims.

Example 1

Generation of JUMP-IN T-REX U2-OS Cell Lines and Targatable JUMP-IN U2-OS Cell Lines Generation of JUMP-IN T-REX U2-OS Cell Lines.

JUMP-IN U2-OS cells were transfected with the pLenti TR puro vector using LIPOFECTAMINE LTX reagent (Life Technologies #15338-100). Transfected cells were selected with 1 μg of puromycin (Life Technologies # A1113803), and the non-transfected parental cells were used as an antibiotic-selection negative control.

The selected clones were expanded and transiently transfected with the PJTI-R4 EXP CMV TO GFP pA vector (Life Technologies). The cells were then tested for tet-repression and tet-inducibility with or without 1 μg of doxycycline, and GFP expression levels were quantified with a Safire II microplate reader.

Eighty four clones survived after the FACS sort. Each clone was plated in triplicate in 96-well plates. One well was used for maintenance, and the other two wells were used for transient transfection with a PJTI R4 EXP CMV-TO pA expression vector (Life Technologies) encoding green fluorescent protein (GFP) for 24 hours. Cells were then treated with or without 1 μg doxycycline for 24 hours, followed by GFP quantification. Response ratio was calculated as $$\frac{\text{(reading of positive doxycycline well)}}{\text{reading of negative doxycycline well}}$$

Twelve JUMP-IN T-REX U2-OS clones with a response ratio over 2 were further expanded. Five of these clones were co-transfected with the R4 integrase construct and PJTI-R4 EXP CMV-TO GFP vector (providing inducible GFP expression). Cells co-transfected with a CMV-GFP construct (providing constitutive GFP expression) and the R4 integrase construct were used as a positive control for transfection and antibiotic selection. After selection with 5 μg/mL of blasticidin for 28 days, cells that were retargeted with the PJTI-R4 EXP CMV-TO GFP vector were induced with 1 μg/mL of doxycycline for 20 hours and then analyzed by FACS.

Generation of Targetable JUMP-IN U2-OS Cell Lines.

Targetable JUMP-IN cell lines were engineered using the JUMP-IN TI Platform Kit (Life Technologies). The PJI PhiC31 Int vector was co-transfected into U2-OS host cells using a PJTI/Blasticidin targeting vector, which contains ATT sites which are complementary to pseudo-ATT sites in the mammalian host genome. Homologous recombination between the ATT sites of the R4 vector and the host genome are facilitated by the phiC31 integrase. The PJI targeting vector contains the hygromycin resistance gene, which permits selection of cells containing stable genomic integrations. These cells were then cloned by flow cytometry and tested to determine the number of R4 sites present in the host cell genome by Southern blot analysis.

Clones with validated single R4 integration sites were validated for retargeting by transfection with the PJTI-R4 EXP CMV-TO-EmGFP-pA and JTI R4 integrase vectors, followed by antibiotic selection for 4 weeks. Clones were plated at 60-80% confluency in a 6-well dish in growth medium without antibiotics (McCoy's 5 A plus 10% dialyzed fetal bovine serum, HEPES, non-essential amino acids, and sodium pyruvate) and transfected with a 1:1 ratio of PJTI-R4 EXP CMV-TO-EmGFP-pA and JTI R4 integrase vectors (2.5 μg DNA total) with LIPOFECTAMINE LTX (6.25 μl) and PLUS Reagent (2.5 μl). The CMV-GFP positive control was introduced into the cells in parallel. Following overnight incubation, the cells were selected for 28 days with 5 μg/mL of blasticidin in growth medium (McCoy's 5 A plus 10% dialyzed FBS, HEPES, non-essential amino acids, sodium pyruvate, and penicillin/streptomycin). After 28 days of antibiotic selection, the selected pools were analyzed by FACS.

Five clones were chosen to test retargeting efficiency and inducible potential. All clones were retargeted successfully. The two clones which had the best retargeting efficiency were further tested for inducible potential by doxycycline. One clone demonstrated ~88% GFP cells in the GFP retargeted control cells and responded very well to doxycycline induction with >99% GFP positive population in the induced culture and only ~4% of GFP positive cells in the non-induced culture. The other clone also responded well to doxycyline induction with >99% GFP positive cells in the induced culture and only ~8% of GFP positive cells in the non-induced culture; with 64% of cells were GFP positive in the GFP retargeted control cells.

Cell Culture Medium.

The table below lists the components of the medium used for JUMP-IN T-REX U2-OS cell culture (Life Technologies):

| Cell Culture Medium and Reagents | Amount | Cat. No. |
|---|---|---|
| McCoy's 5A Medium (modified) (1x), Liquid | 500 mL | 16600-082 |
| Fetal bovine serum (FBS), dialyzed | 100 mL | 26400-036 |
| Penicillin/Streptomycin, 10,000 U/10,000 pg | 100 mL | 15140-122 |
| Hygromycin B (50 mg/mL) | 20 mL | 10687-010 |
| Puromycin Dihydrochloride (10 mg/mL) | 1 mL | A11138-03 |
| Phosphate-buffered saline without calcium or magnesium | 1000 mL | 14190-136 |

Example 2

Methods

Cell Culture and Compound Treatment.

U2-OS cells were grown in McCoy media supplemented with 10% fetal bovine serum. Cells were seeded at density of 5,000 cells/well on PDL-coated 384-well plates.

BacMam Transfection.

U2-OS cells were transiently transfected with 0.5-12 μl of BacMam encoding G protein, gustducin (Gα15, Gα16gust44) per 40,000 cells during 24 h or 48 h. Transfected cells were seeded at density of 5,000 cells/well on PDL-coated 384-well plates.

Functional Expression.

JUMP-IN T-REX U2-OS cells were transfected with the PJTI-R4EXP-CMV-TO-T1R3/T1R2/Gα15-pA and JTI-R4 Integrase vectors (Life Technology). Doxycycline-induced expression of T1R3/T1R2/Gα15 was detected by RT-PCR.

pERK1/2 Assay.

For pERK1/2 studies, growth media was replaced with media without serum for 2 h. U2-OS cells were treated with 100 mM Sweet compounds with or without of U73122 (10 μM) and with or without lactisole (20 mM). Control groups of cells also received DMSO (0.1%) in medium. The fixed cells were stained with rabbit anti-phospho-p44/p42 MAPK (pERK1/2) antibodies from Cell Signaling Technologies, then with secondary Alexa 488-conjugated antibodies (Life Technology) and HOECHST 33342. Images were acquired on an ImageXpressMicro (MDC) and analyzed with MWCS Module.

Calcium Assay.

Calcium traces in Fluo-4AM loaded cells were recorded over time in FLIPR$^{Tetra}$ (MDC) with $\lambda_{EX}$=470-495 nm and $\lambda_{EM}$=515-575 nm. The peak increase in fluorescence over baseline was determined and is expressed as relative fluorescence units (RFU).

TRANSFLUOR Model.

TRANSFLUOR U2-OS cells stably expressing β-arrestin-GFP were transiently transfected with taste G protein, gustducin (Gα15 or Gα16gust44) (Life Technologies) or were transiently transfected with sweet receptor T1R2/T1R3 and taste G protein. Treatment of cells with sweet-tasting compounds induced formation of fluorescent vesicles. Sweet receptor internalization was quantitated via the TRANSFLUOR Application Module of the METAXPRESS Software (MDC).

Example 3

Phosphorylation of ERK1/2

Figure 4:
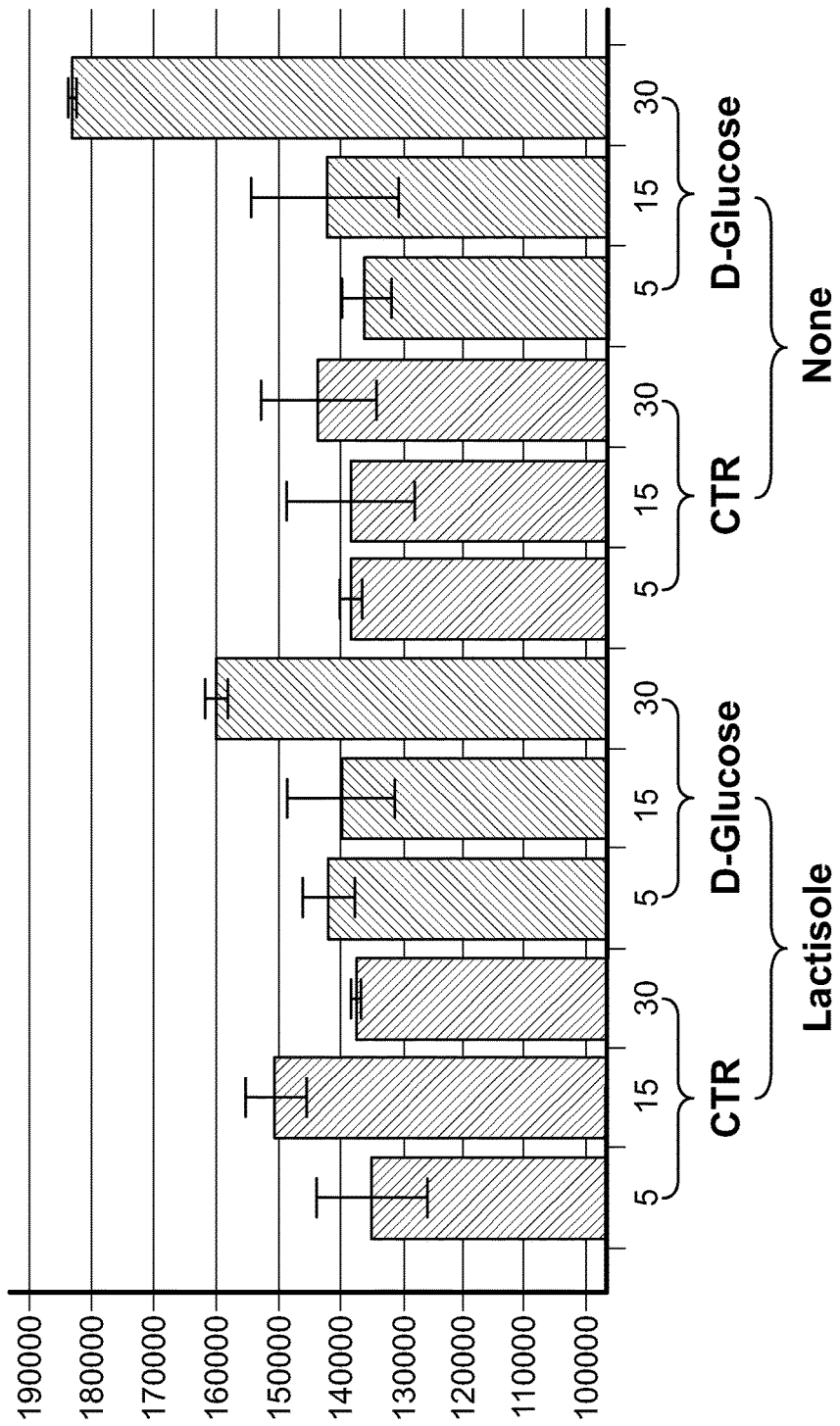
Figure 5:
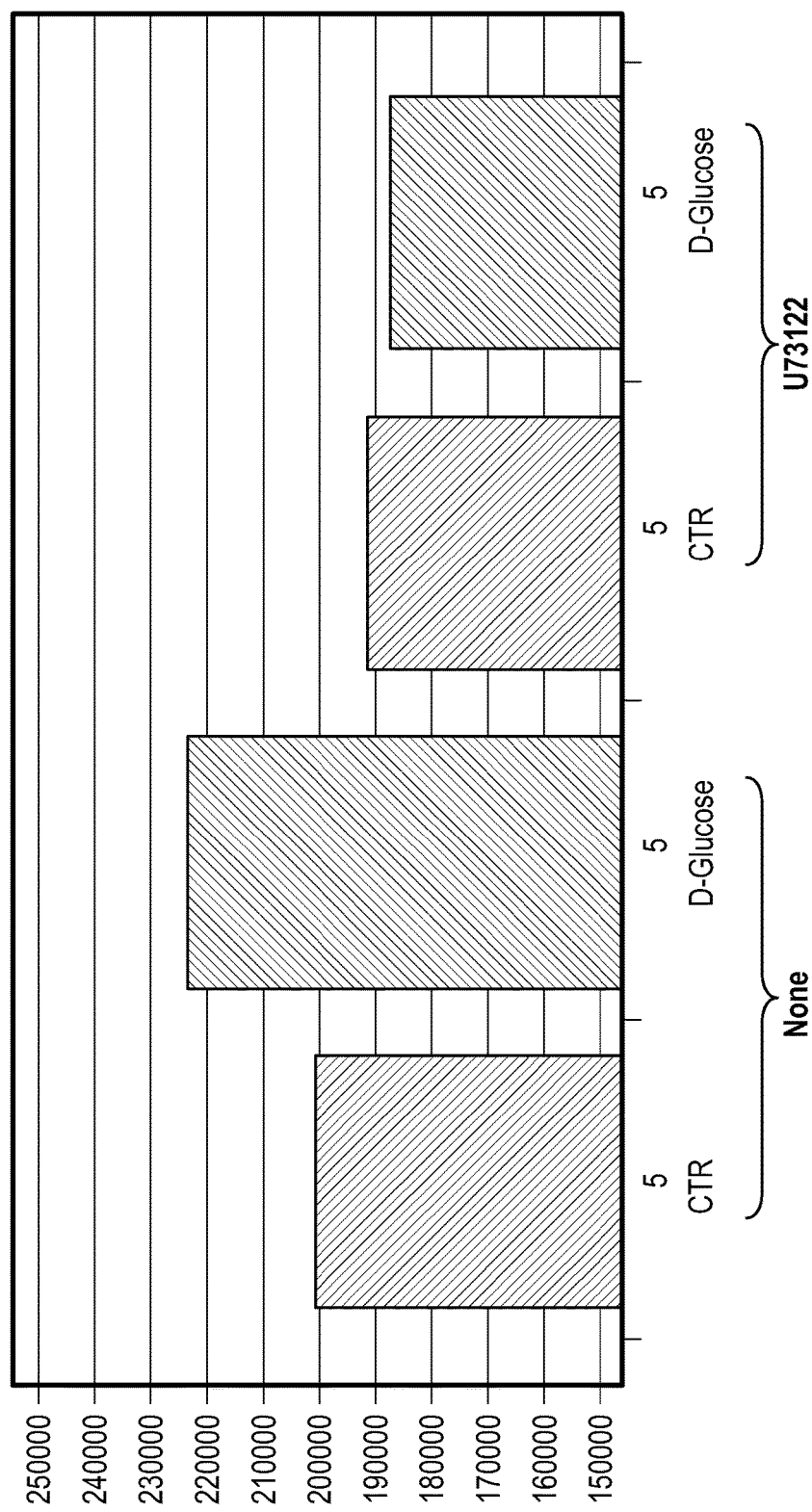

The phosphorylation of ERK1/2 is a common downstream event following GPCR activation via the PLCβ2-IP3 pathway. Growth media was replaced with Dulbecco's phosphate buffered saline (DPBS) without serum for 2 h. U2-OS cells were treated with 100 mM D-glucose with or without of 20 mM of lactisole for 5, 15 and 30 minutes and then fixed and stained with anti-pERK1/2 and HOECHST 33342 before imaging. pERK1/2 expression was quantitated using Molecular Devices' Multiwaves Cell Scoring analysis algorithm. For each data point, average of Mean Cell Integrated intensity and standard deviation are calculated from quadruplicate data points. D-glucose induced pERK1/2 activation in a time-dependent manner in parental U2-OS (FIG. 4, left) and in U2-OS cells overexpressing Gα15 (FIG. 5, left). Importantly, pERK1/2 activity was blocked by the sweet receptor antagonist, lactisole (FIG. 4, right) or the PLCβ2 inhibitor U73122 (FIG. 5, right).

Example 4

Overexpression of Gα15

Figure 2:
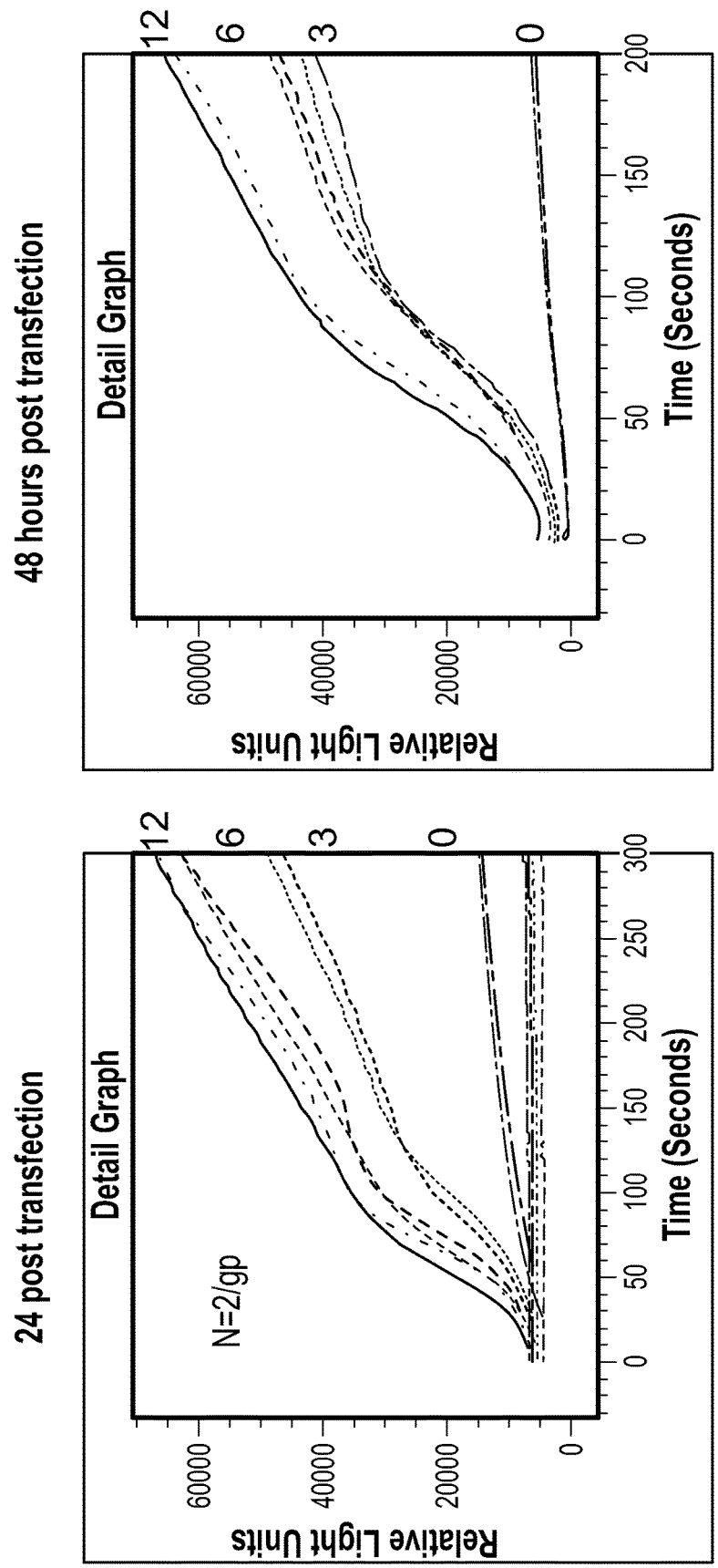
Figure 3:
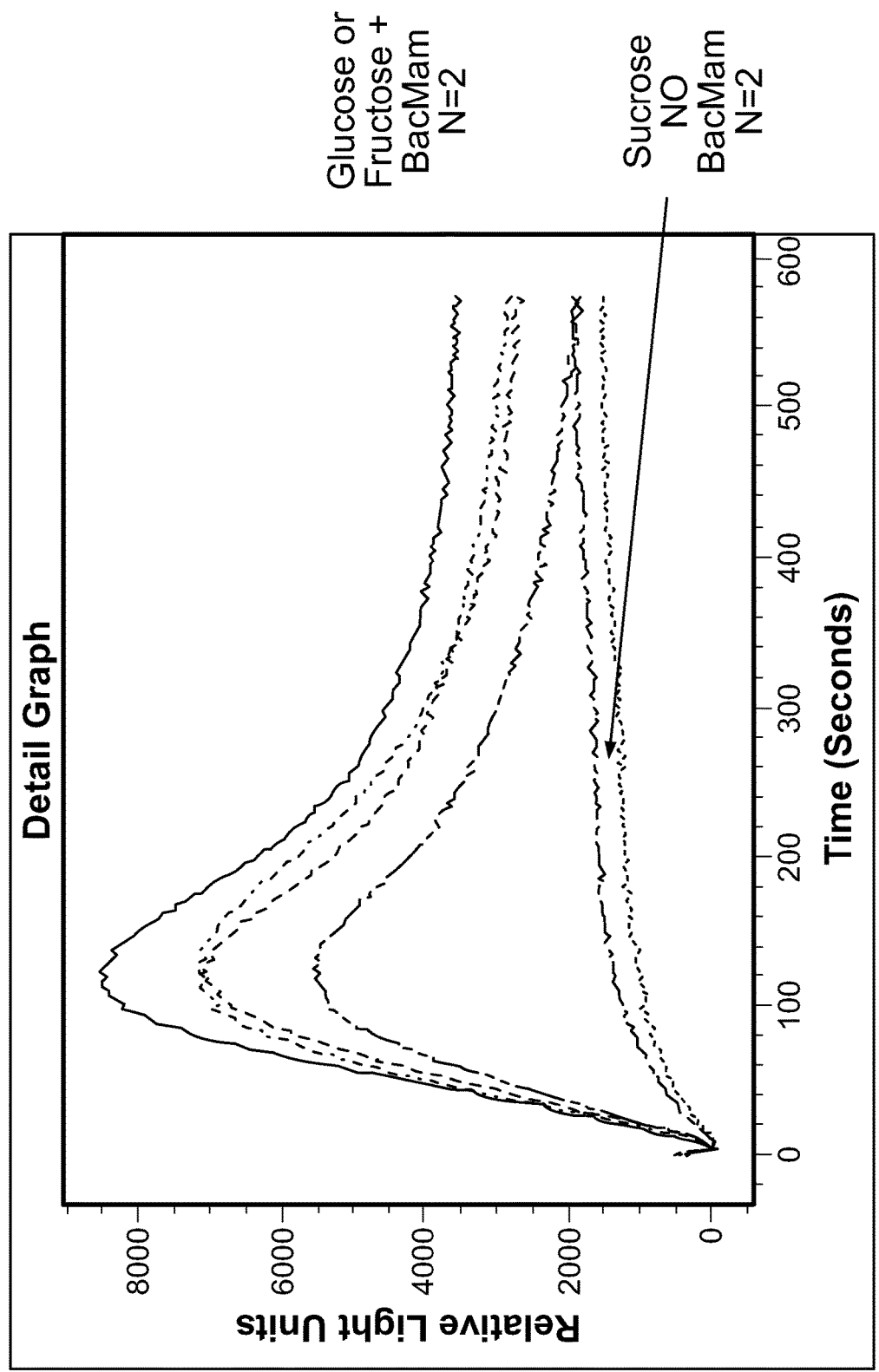
Figure 6:
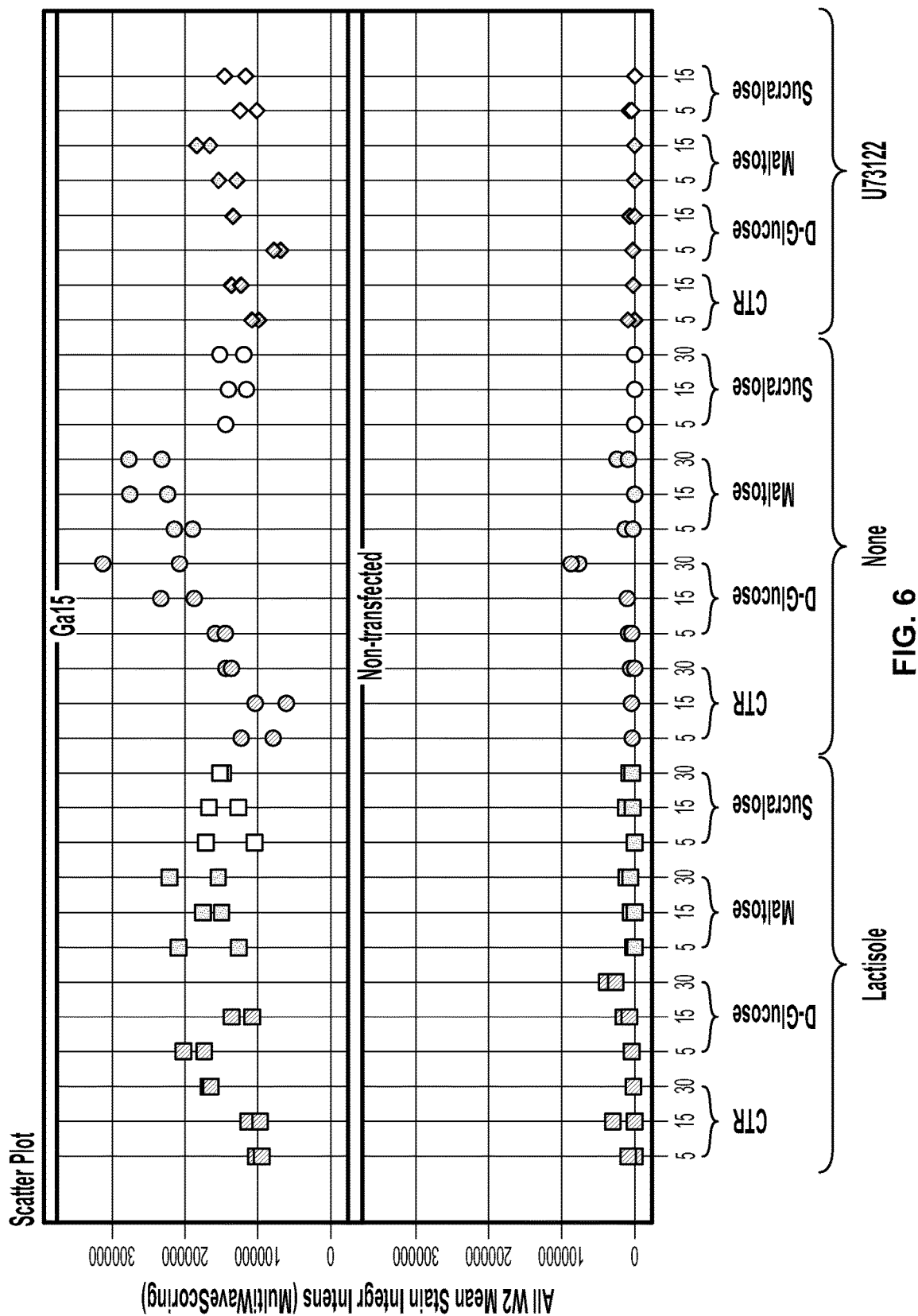
Figure 7:
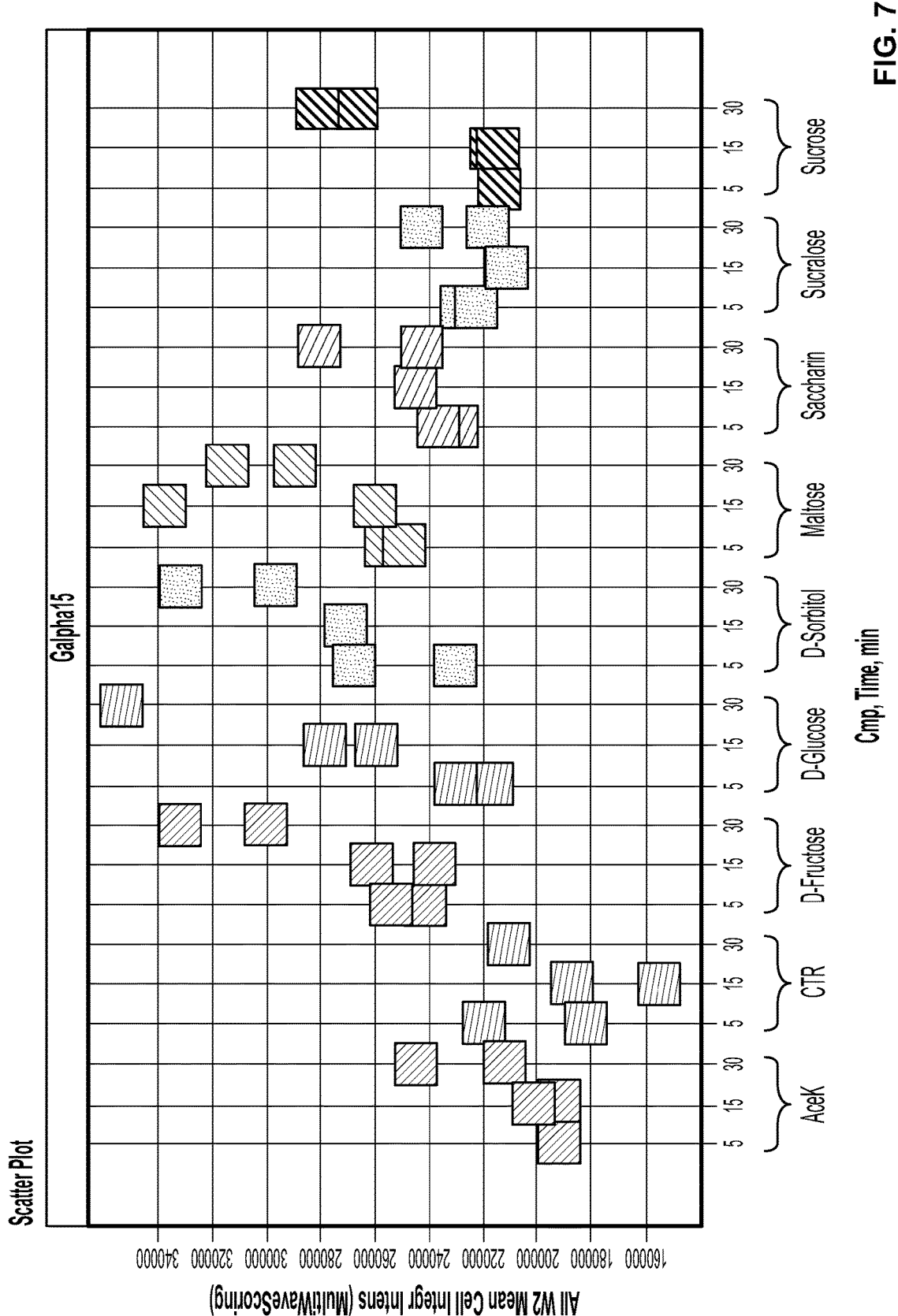

Overexpression of Gα15 in a U2-OS cell significantly increases signaling in response to a sweet taste modulator. Sucralose induced $Ca^{(2+)}$ response in U2-OS cell line transfected with Gα15 in concentration-dependent manner (FIG. 2). We observed the highest $Ca^{(2+)}$ response in U2-OS cells transfected with 12 μl/40,000 cells (FIG. 2). Transfection of U2-OS cells with 6 μl/40,000 cells significantly increased $Ca^{(2+)}$ response upon treatment with natural sugars, such as glucose, fructose, and sucrose (FIG. 3). Furthermore, overexpression of Gα15 increased pERK1/2 activity upon treatment with glucose, or maltose in U2-OS cells (FIG. 6). Importantly pERK1/2 activation was blocked by PLCβ2 inhibitor U73122 (FIG. 7).

Example 5

$Ca^{(2+)}$ Response

Figure 1B:
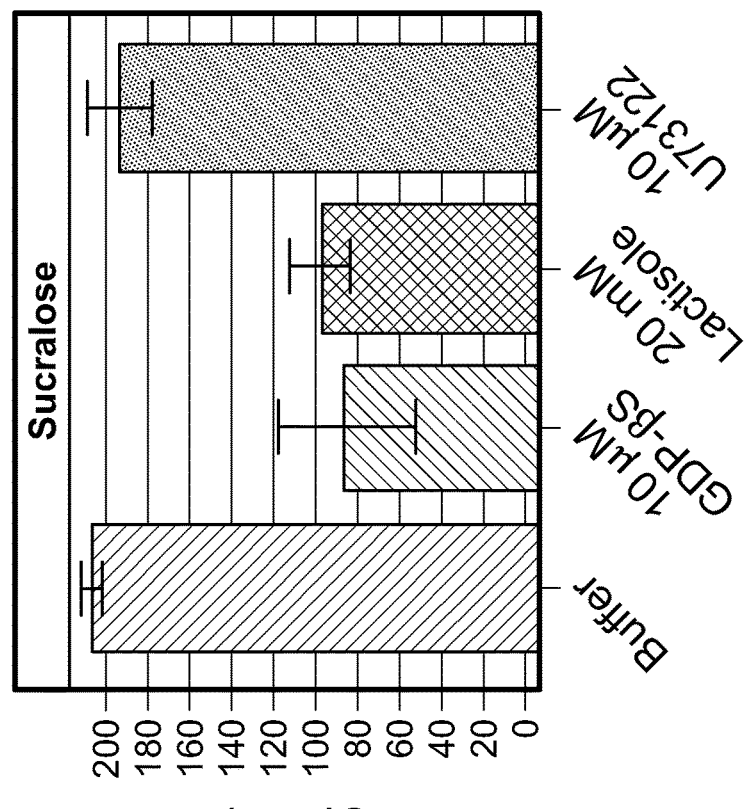
Figure 1B:
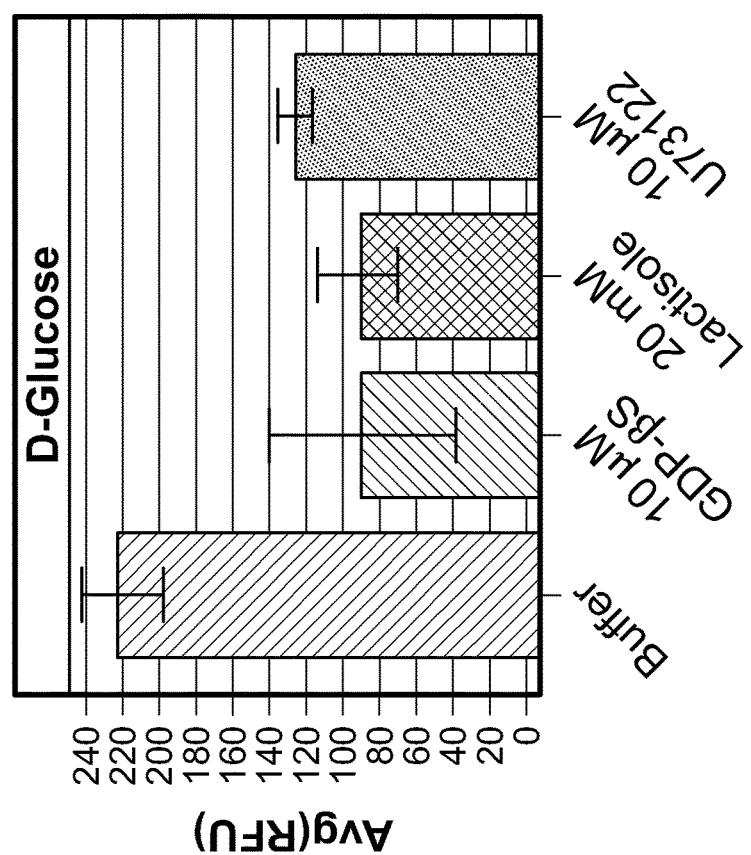

We have found that both monosaccharaides and disaccharides induced a concentration-dependent $Ca^{(2+)}$ response in JUMP-IN T-REX U2-OS cell line with doxycycline-inducible expression of sweet taste receptor T1R2/T1R3/Gα15 (FIG. 1A). T1R2/T1R3-mediated $Ca^{(2+)}$ release was inhibited by lactisole (FIG. 1B). Moreover, U73122 abolished $Ca^{(2+)}$ release upon treatment with D-glucose and D-fructose and had no effect on $Ca^{(2+)}$ response after stimulation with sucrose and sucralose (FIG. 1B).

Taken together, these data demonstrate a relationship between the molecular structure of sugars and the T1R2/T1R3 sweet taste receptor.

Example 6

Artificial Sweeteners

Some striking observations were made with the artificial sweeteners, Ace-K, aspartame, and saccharine. Ace-K and aspartame did not induce T1R2/T1R3-mediated $Ca^{(2+)}$ response in JUMP-IN T-REX U2-OS cells (FIG. 1A). T1R2/T1R3-independent $Ca^{(2+)}$ release occurred upon treatment with saccharine (FIG. 1A), indicating that artificial sweeteners Ace-K, aspartame, and saccharine target common receptor which was yet to be identified.

Example 7

Figure 8A:
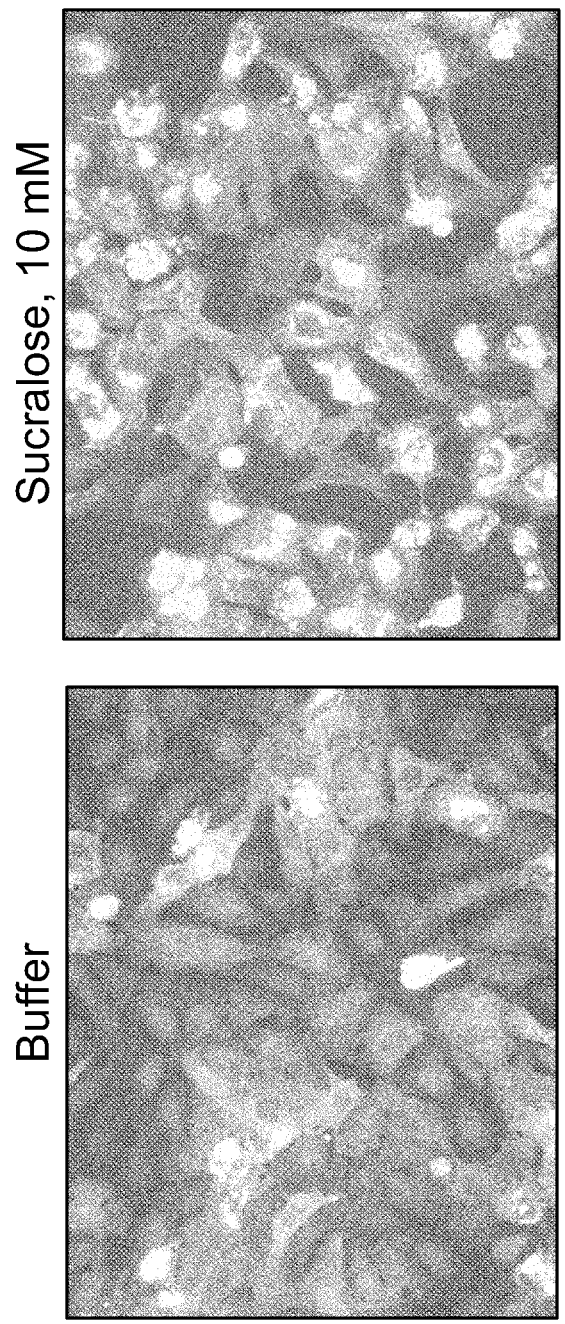
Figure 8B:
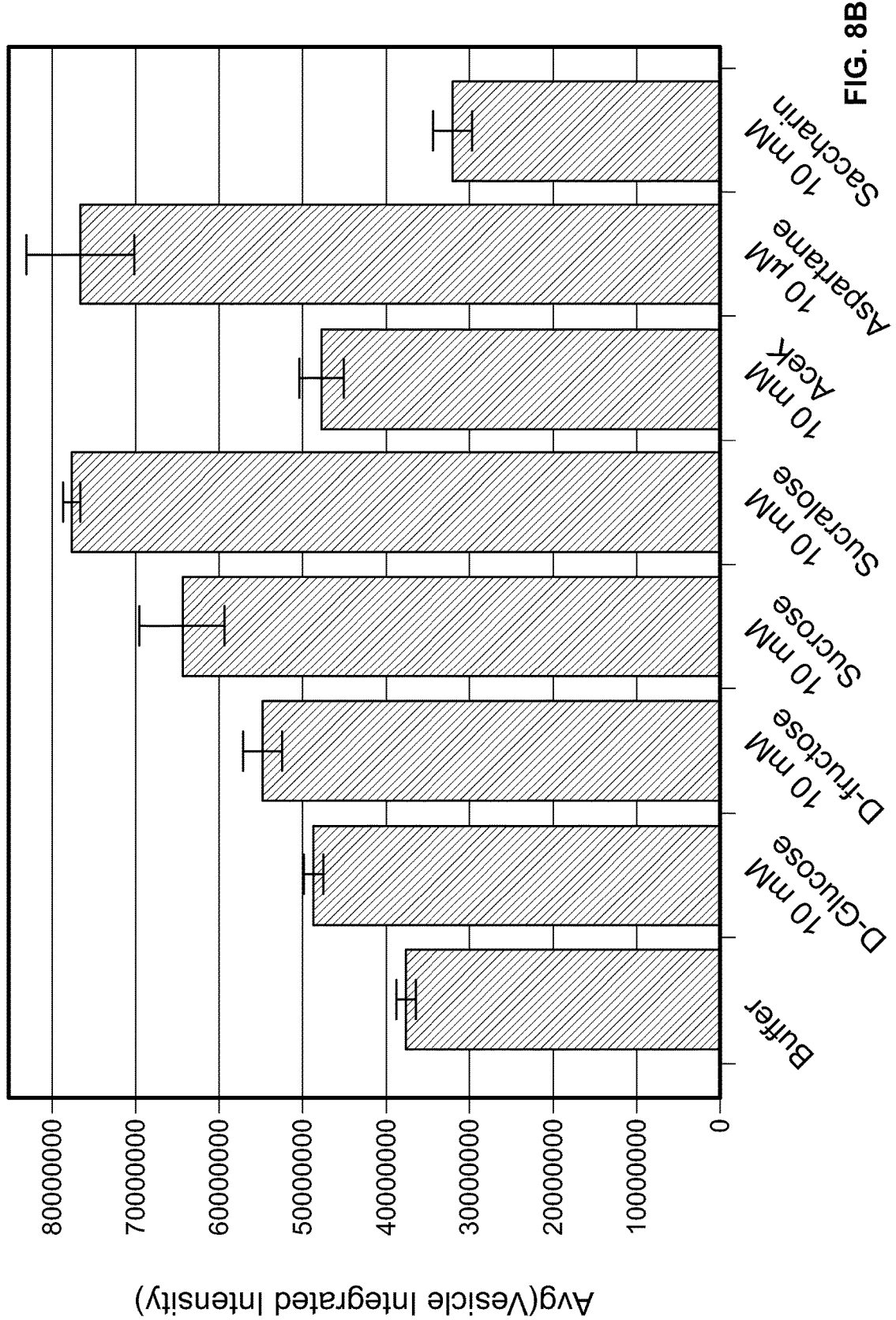
Figures 9A, 9B:
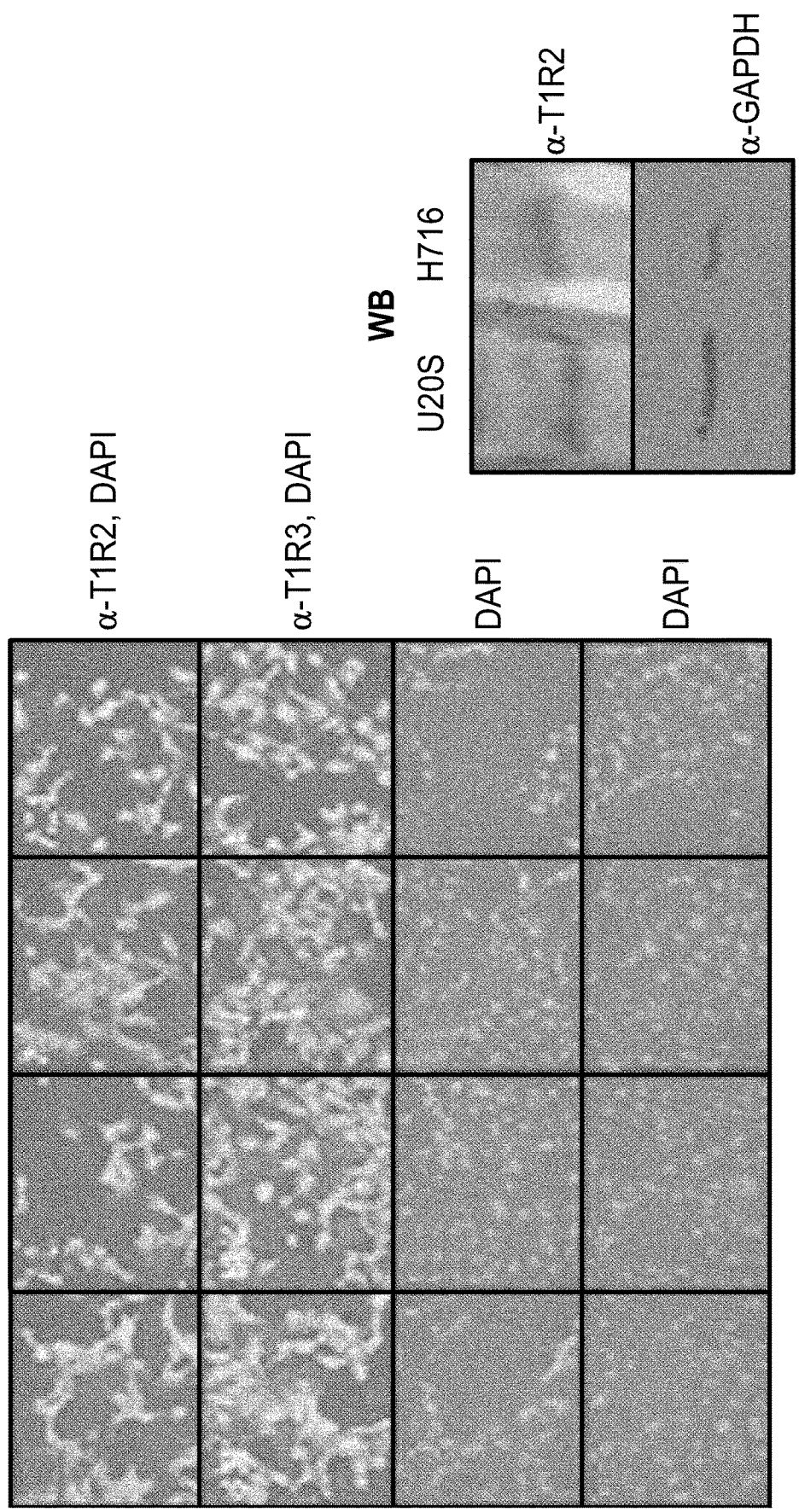

Effects of Sweet-Tasting Compounds on Recruiting β-Arrestin to Sweet Taste Receptor Multiple lines of evidence suggested that GPCR ligands selectively activate β-arrestin signaling pathway. To assess the effects of sweet-tasting compounds on recruiting β-arrestin to sweet taste receptor, we used a TRANSFLUOR Model (MDC), which is highly sensitive to β-arrestin redistribution. Treatment of cells with sweet-tasting compounds induced formation of fluorescent vesicles, indicating internalization of T1R2/T1R3-β-arrestin complexes into endosomes (FIG. 8A). Sweet receptor internalization was quantitated via the TRANSFLUOR Application Module of the METAXPRESS Software (MDC). D-glucose, D-fructose, and Ace-K slightly increased sweet receptor internalization, whereas sucrose, sucralose, and aspartame had strong effect on T1R2/T1R3 internalization (FIG. 8B). In contrast, even minimal internalization did not occur upon treatment with saccharine (FIG. 8B).

The invention claimed is:

1. An isolated U2-OS cell, comprising a T1R2/T1R3 sweet taste receptor and an exogenous nucleic acid sequence encoding Gα16gust25, Gα15gust25, Gα15gust44, or Gα15-i/3-5.

2. An isolated U2-OS cell, comprising:
   one or more exogenous nucleic acid sequences encoding a T1R2/T1R3 sweet taste receptor; and
   an exogenous nucleic acid sequence encoding Gα16gust25, Gα15gust25, Gα15gust44, and Gα15-i/3-5.

3. The isolated U2-OS cell of claim 1 or 2, further comprising an exogenous nucleic acid sequence encoding a detectable label.

4. The isolated U2-OS cell of claim 3, wherein the detectable label is β-arrestin GFP.

5. A method of identifying a sweet taste modulator comprising:
   a) contacting a U2-OS cell comprising a T1R2/T1R3 sweet taste receptor with a sweetener and a test compound, wherein the U2-OS cell expresses or overexpresses a Gα protein selected from the group consisting of Gα16gust25, Gα15gust25, Gα15gust44, and Gα15-i/3-5; and
   b) measuring sweet taste receptor activity, wherein a change in sweet taste receptor activity by the sweetener in the presence of the test compound indicates that the test compound is a sweet taste modulator;
   wherein, in the presence of a sweet taste receptor antagonist, the change in sweet taste receptor activity is blocked.

6. The method of claim 5, wherein the U2-OS cell is modified to overexpress the sweet taste receptor.

7. The method of claim 5, wherein the sweet taste receptor activity is measured by detecting the level of an intracellular second messenger in the U2-OS cell.

8. The method of claim 7, wherein the second messenger is cAMP, cGMP, NO, CO, or H2S.

9. The method of claim 7, wherein the second messenger is DAG or IP3.

10. The method of claim 5, wherein sweet taste receptor activity is measured by detecting the level of intracellular calcium in the cell.

11. The method of claim 5, wherein the sweet taste receptor activity is binding activity of the sweet taste receptor to the sweetener.

12. The method of claim 11, wherein a change in binding activity of the sweet taste receptor to the sweetener is detected by a competitive binding assay.

13. The method of claim 11, wherein a change in binding activity of the sweet taste receptor to the sweetener is detected by surface plasmon resonance.

14. The method of claim 5, wherein sweet taste receptor activity is measured by detecting phosphorylation of ERK 1/2.

15. The method of claim 5, wherein sweet taste receptor activity is measured by detecting internalization of the receptor.

16. The method of any of claims 5-15, wherein the U2-OS cell further comprises a Tet-repressor protein expression construct.

17. The method of claim 5, wherein the sweet taste receptor antagonist is lactisole.

18. The method of claim 5, wherein Gα16gust25 is encoded by SEQ ID NO: 3.

19. The method of claim 5, wherein Gα15gust25 is encoded by SEQ ID NO: 5.

20. The method of claim 5, wherein Gα15gust44 is encoded by SEQ ID NO: 7.

21. The method of claim 5, wherein Gα15-i/3-5 is encoded by SEQ ID NO: 8.

* * * * *